US011213319B2

(12) United States Patent
Hart et al.

(10) Patent No.: US 11,213,319 B2
(45) Date of Patent: *Jan. 4, 2022

(54) TROCAR SURGICAL SEAL

(71) Applicant: Applied Medical Resources Corporation, Rancho Santa Margarita, CA (US)

(72) Inventors: Charles C. Hart, Rancho Santa Margarita, CA (US); John R. Brustad, Rancho Santa Margarita, CA (US); Jeremy J. Albrecht, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 329 days.

This patent is subject to a terminal disclaimer.

(21) Appl. No.: 16/537,265

(22) Filed: Aug. 9, 2019

(65) Prior Publication Data

US 2019/0357938 A1 Nov. 28, 2019

Related U.S. Application Data

(63) Continuation of application No. 15/237,184, filed on Aug. 15, 2016, now abandoned, which is a
(Continued)

(51) Int. Cl.
*A61B 17/34* (2006.01)
*A61B 17/02* (2006.01)

(52) U.S. Cl.
CPC ...... *A61B 17/3439* (2013.01); *A61B 17/0218* (2013.01); *A61B 17/0293* (2013.01);
(Continued)

(58) Field of Classification Search
CPC ........ A61B 17/0218; A61B 2017/0225; A61B 17/0293; A61B 17/3423;
(Continued)

(56) References Cited

U.S. PATENT DOCUMENTS 1,157,202 A  10/1915 McLeland et al.
4,640,273 A   2/1987 Greene et al.
(Continued)

FOREIGN PATENT DOCUMENTS

EP       1 698 291       9/2006
WO    WO2001/026559    4/2001
(Continued)

OTHER PUBLICATIONS

European Patent Office, The International Search Report and Written Opinion for International Application No. PCT/US2014/028892, dated Jun. 24, 2014, entitled "Trocar Surgical Seal".
(Continued)

*Primary Examiner* — Samuel S Hanna
(74) *Attorney, Agent, or Firm* — Patrick Ikehara

(57) ABSTRACT

A trocar surgical seal or surgical access device is provided. The trocar surgical seal comprises first and second supports coupled together by a film passageway. The trocar surgical seal provides an instrument seal for instruments inserted therethrough. The trocar surgical seal occupies minimal surgical space.

10 Claims, 23 Drawing Sheets

Related U.S. Application Data continuation of application No. 14/213,602, filed on Mar. 14, 2014, now Pat. No. 9,421,034.

(60) Provisional application No. 61/790,258, filed on Mar. 15, 2013.

(52) U.S. Cl.
CPC ...... *A61B 17/3423* (2013.01); *A61B 17/3462* (2013.01); *A61B 2017/0225* (2013.01); *A61B 2017/3441* (2013.01); *A61B 2017/3445* (2013.01); *A61B 2017/3466* (2013.01)

(58) Field of Classification Search
CPC .... A61B 2017/3441; A61B 2017/3445; A61B 17/3439; A61B 17/3462; A61B 2017/3466; A61B 2017/3449; A61B 2017/3447

See application file for complete search history.

(56) References Cited

U.S. PATENT DOCUMENTS

| | | | |
|---|---|---|---|
| 4,950,223 A | 8/1990 | Silvanov |
| 4,984,564 A | 1/1991 | Yuen |
| 5,144,942 A | 9/1992 | Decarie et al. |
| 5,201,714 A | 4/1993 | Gentelia et al. |
| 5,308,336 A | 5/1994 | Hart et al. |
| 5,342,315 A | 8/1994 | Rowe et al. |
| 5,342,385 A | 8/1994 | Norelli |
| 5,360,417 A | 11/1994 | Gravener et al. |
| 5,366,478 A | 11/1994 | Brinkerhoff |
| 5,429,609 A | 7/1995 | Yoon |
| 5,441,486 A | 8/1995 | Yoon |
| 5,514,133 A | 5/1996 | Golub |
| 5,524,644 A | 6/1996 | Crook |
| 5,649,550 A | 7/1997 | Crook |
| 5,752,938 A | 5/1998 | Flatland et al. |
| 5,782,817 A | 7/1998 | Franzel et al. |
| 5,788,676 A | 8/1998 | Yoon |
| 5,810,721 A | 9/1998 | Mueller |
| 5,813,409 A | 9/1998 | Leahy |
| 5,832,925 A | 11/1998 | Rothrum |
| 5,853,395 A | 12/1998 | Crook |
| 5,865,807 A | 2/1999 | Blake, III |
| 5,906,577 A | 5/1999 | Beane |
| 5,989,233 A | 11/1999 | Yoon |
| 5,993,485 A | 11/1999 | Beckers |
| 6,007,544 A | 12/1999 | Ducksoo |
| 6,033,426 A | 3/2000 | Kaji |
| 6,033,428 A | 3/2000 | Sardella |
| 6,048,309 A | 4/2000 | Flom |
| 6,077,288 A | 6/2000 | Shimomura |
| 6,110,154 A | 8/2000 | Shimomura |
| 6,142,935 A | 11/2000 | Flom |
| 6,142,936 A | 11/2000 | Beane |
| 6,238,373 B1 | 5/2001 | De la Torre et al. |
| 6,254,533 B1 | 7/2001 | Fadem |
| 6,254,534 B1 | 7/2001 | Butler |
| 6,382,211 B1 | 5/2002 | Crook |
| 6,440,063 B1 | 8/2002 | Beane |
| 6,450,983 B1 | 9/2002 | Rambo |
| 6,485,467 B1 | 11/2002 | Crook et al. |
| 6,582,364 B2 | 6/2003 | Butler |
| 6,589,167 B1 | 7/2003 | Shimomura |
| 6,613,952 B2 | 9/2003 | Rambo |
| 6,723,044 B2 | 4/2004 | Pulford |
| 6,814,078 B2 | 11/2004 | Crook |
| 6,814,700 B1 | 11/2004 | Mueller |
| 6,846,287 B2 | 1/2005 | Bonadio |
| 6,945,932 B1 | 9/2005 | Caldwell |
| 6,958,037 B2 | 10/2005 | Ewers |
| 7,008,377 B2 | 3/2006 | Beane |
| 7,041,056 B2 | 5/2006 | Deslauriers |
| 7,081,089 B2 | 7/2006 | Bonadio |
| 7,153,261 B2 | 12/2006 | Wenchell |
| 7,195,590 B2 | 3/2007 | Butler |
| 7,214,185 B1 | 5/2007 | Rosney |
| 7,294,103 B2 | 11/2007 | Bertolero |
| 7,297,106 B2 | 11/2007 | Yamada |
| 7,300,399 B2 | 11/2007 | Bonadio |
| 7,390,317 B2 | 6/2008 | Taylor et al. |
| 7,393,322 B2 | 7/2008 | Wenchell |
| 7,445,597 B2 | 11/2008 | Butler |
| 7,473,221 B2 | 1/2009 | Ewers et al. |
| 7,481,765 B2 | 1/2009 | Ewers et al. |
| 7,537,564 B2 | 5/2009 | Bonadio |
| 7,540,839 B2 | 6/2009 | Butler |
| 7,559,893 B2 | 7/2009 | Bonadio |
| 7,650,887 B2 | 1/2010 | Nguyen et al. |
| 7,678,046 B2 | 3/2010 | White |
| 7,686,823 B2 | 3/2010 | Pingleton et al. |
| 7,717,847 B2 | 5/2010 | Smith |
| 7,749,161 B2 | 7/2010 | Beckman |
| 7,753,901 B2 | 7/2010 | Piskun et al. |
| 7,758,500 B2 | 7/2010 | Boyd |
| 7,766,822 B2 | 8/2010 | White |
| 7,766,824 B2 | 8/2010 | Jensen |
| 7,819,800 B2 | 10/2010 | Beckman |
| 7,931,623 B2 | 4/2011 | Wing et al. |
| 7,998,068 B2 | 8/2011 | Bonadio et al. |
| 2001/0037053 A1 | 11/2001 | Bonadio |
| 2002/0002324 A1 | 1/2002 | McManus |
| 2003/0187376 A1 | 10/2003 | Rambo |
| 2003/0192553 A1 | 10/2003 | Rambo |
| 2004/0092796 A1 | 5/2004 | Butler |
| 2004/0106942 A1 | 6/2004 | Taylor et al. |
| 2004/0154624 A1 | 8/2004 | Bonadio |
| 2004/0167559 A1 | 8/2004 | Taylor et al. |
| 2004/0215063 A1 | 10/2004 | Bonadio |
| 2004/0254426 A1 | 12/2004 | Wenchell |
| 2005/0148823 A1 | 7/2005 | Vaugh |
| 2005/0155611 A1 | 7/2005 | Vaugh |
| 2005/0192483 A1 | 9/2005 | Bonadio et al. |
| 2005/0203346 A1 | 9/2005 | Bonadio |
| 2005/0209510 A1 | 9/2005 | Bonadio |
| 2005/0209627 A1 | 9/2005 | Kick et al. |
| 2005/0261720 A1 | 11/2005 | Caldwell |
| 2006/0142642 A1 | 6/2006 | Lins |
| 2006/0161049 A1 | 7/2006 | Beane |
| 2006/0161050 A1 | 7/2006 | Butler |
| 2006/0247498 A1 | 11/2006 | Bonadio |
| 2006/0247500 A1 | 11/2006 | Voegele |
| 2007/0051375 A1 | 3/2007 | Milliman |
| 2007/0055107 A1 | 3/2007 | Wenchell |
| 2007/0088241 A1 | 4/2007 | Brustad et al. |
| 2007/0093695 A1 | 4/2007 | Bonadio |
| 2007/0203398 A1 | 8/2007 | Bonadio |
| 2007/0239108 A1 | 10/2007 | Albrecht et al. |
| 2007/0270752 A1 | 11/2007 | Labombard |
| 2007/0299314 A1 | 12/2007 | Bertolero |
| 2008/0011307 A1 | 1/2008 | Beckman |
| 2008/0021362 A1 | 1/2008 | Fihe |
| 2008/0051733 A1 | 2/2008 | Lynn |
| 2008/0091080 A1 | 4/2008 | Leahy |
| 2008/0091143 A1 | 4/2008 | Taylor et al. |
| 2008/0097162 A1 | 4/2008 | Bonadio |
| 2008/0097163 A1 | 4/2008 | Butler |
| 2008/0146882 A1 | 6/2008 | Cropper |
| 2008/0146883 A1 | 6/2008 | Kistler |
| 2008/0208222 A1 | 8/2008 | Beckman |
| 2008/0249371 A1 | 10/2008 | Beckman |
| 2008/0249373 A1 | 10/2008 | Wenchell |
| 2008/0300467 A1 | 12/2008 | Schaefer |
| 2009/0024097 A1 | 1/2009 | Okoniewski |
| 2009/0030375 A1 | 1/2009 | Franer et al. |
| 2009/0036745 A1 | 2/2009 | Bonadio |
| 2009/0082631 A1 | 3/2009 | Cronin |
| 2009/0082632 A1 | 3/2009 | Voegele |
| 2009/0118587 A1 | 5/2009 | Voegele |
| 2009/0149714 A1 | 6/2009 | Bonadio |
| 2009/0182282 A1 | 7/2009 | Okihisa et al. |
| 2009/0187079 A1 | 7/2009 | Albrecht et al. |
| 2009/0227843 A1 | 9/2009 | Smith |

(56) References Cited

U.S. PATENT DOCUMENTS

| | | |
|---|---|---|
| 2009/0281500 A1 | 11/2009 | Acosta et al. |
| 2009/0292176 A1 | 11/2009 | Bonadio |
| 2009/0306586 A1 | 12/2009 | Ross et al. |
| 2009/0326330 A1 | 12/2009 | Bonadio |
| 2009/0326332 A1 | 12/2009 | Carter |
| 2010/0030032 A1 | 2/2010 | Voegele |
| 2010/0063362 A1 | 3/2010 | Bonadio |
| 2010/0081880 A1 | 4/2010 | Widenhouse |
| 2010/0081881 A1 | 4/2010 | Murray |
| 2010/0081882 A1 | 4/2010 | Hess |
| 2010/0081995 A1 | 4/2010 | Widenhouse |
| 2010/0094227 A1 | 4/2010 | Albrecht et al. |
| 2010/0113882 A1 | 5/2010 | Widenhouse |
| 2010/0113883 A1 | 5/2010 | Widenhouse |
| 2010/0145152 A1 | 6/2010 | Smith |
| 2010/0185057 A1 | 7/2010 | Stearns |
| 2010/0204548 A1 | 8/2010 | Bonadio |
| 2010/0217087 A1 | 8/2010 | Bonadio |
| 2010/0228090 A1 | 9/2010 | Weisenburgh, II |
| 2010/0228091 A1 | 9/2010 | Widenhouse |
| 2010/0228092 A1 | 9/2010 | Ortiz |
| 2010/0228094 A1 | 9/2010 | Ortiz |
| 2010/0240960 A1 | 9/2010 | Richard |
| 2010/0249516 A1 | 9/2010 | Shelton, IV |
| 2010/0249520 A1 | 9/2010 | Shelton, IV |
| 2010/0249521 A1 | 9/2010 | Shelton, IV |
| 2010/0249525 A1 | 9/2010 | Shelton, IV |
| 2010/0249526 A1 | 9/2010 | Shelton, IV |
| 2010/0249694 A1 | 9/2010 | Choi |
| 2010/0261970 A1 | 10/2010 | Shelton, IV |
| 2010/0261972 A1* | 10/2010 | Widenhouse ...... A61B 17/3462 600/206 |
| 2010/0261974 A1 | 10/2010 | Shelton, IV |
| 2010/0261975 A1 | 10/2010 | Huey |
| 2010/0262080 A1 | 10/2010 | Shelton, IV |
| 2010/0268035 A1 | 10/2010 | Oberländer |
| 2010/0274093 A1 | 10/2010 | Shelton, IV |
| 2010/0280326 A1 | 11/2010 | Hess |
| 2010/0280327 A1 | 11/2010 | Nobis |
| 2010/0280368 A1 | 11/2010 | Can et al. |
| 2010/0280437 A1 | 11/2010 | Murr |
| 2011/0066001 A1 | 3/2011 | Shelton et al. |
| 2011/0172495 A1 | 7/2011 | Armstrong |
| 2011/0251465 A1 | 10/2011 | Kleyman |
| 2012/0095297 A1 | 4/2012 | Dang et al. |
| 2012/0130184 A1 | 5/2012 | Richard |
| 2012/0157781 A1 | 6/2012 | Kleyman |
| 2012/0157782 A1 | 6/2012 | Alfieri |
| 2012/0157783 A1 | 6/2012 | Okoniewski |
| 2012/0157786 A1 | 6/2012 | Pribanic |
| 2012/0245430 A1 | 9/2012 | Kleyman et al. |
| 2012/0253134 A1 | 10/2012 | Smith |
| 2012/0253136 A1 | 10/2012 | Rodrigues |
| 2012/0283519 A1 | 11/2012 | Nguyen et al. |
| 2013/0018230 A1 | 1/2013 | Su et al. |

FOREIGN PATENT DOCUMENTS

| | | |
|---|---|---|
| WO | WO 03/034908 | 5/2003 |
| WO | WO 03/103548 | 12/2003 |
| WO | WO 2004/030547 | 4/2004 |
| WO | WO 2006/082572 | 8/2006 |
| WO | WO2010/045253 | 4/2010 |
| WO | WO2010082722 | 7/2010 |
| WO | WO2010104259 | 9/2010 |
| WO | WO2012/044959 | 4/2012 |

OTHER PUBLICATIONS

The International Bureau of WIPO, International Preliminary Report on Patentability for International Application No. PCT/US2014/028892, titled, Trocar Surgical Seal dated Sep. 24, 2015.

* cited by examiner

TROCAR SURGICAL SEAL

CROSS-REFERENCE TO RELATED APPLICATIONS

This application is a continuation of U.S. application Ser. No. 15/237,184, filed Aug. 15, 2016, which is a continuation of U.S. application Ser. No. 14/213,602, filed Mar. 14, 2014, now U.S. Pat. No. 9,421,034, which claims the benefit of U.S. Provisional Application No. 61/790,258, filed Mar. 15, 2013, the entire disclosure of which is hereby incorporated by reference as if set forth in full herein.

BACKGROUND

This application relates generally to surgical access systems and more specifically to trocars and other such surgical access devices and specifically to laparoscopic surgical access devices for use in minimally invasive surgical procedures and laparoscopic procedures that result in crowded surgical operating fields.

Surgical access devices are commonly used to facilitate the introduction of surgical instruments through body conduits and into body cavities. A trocar is such a surgical access device and is used in laparoscopic procedures to provide access through the abdominal wall and into the abdominal cavity. In laparoscopic surgeries, the abdominal cavity is commonly inflated or insufflated in order to increase the volume of the working environment. Under these circumstances, one or more valves or seals are provided in a seal housing of the trocar to inhibit the escape of the insufflation gas. The valves form an instrument seal in the presence of an instrument, and a zero seal in the absence of an instrument.

Trocar systems have been of particular advantage in facilitating minimally invasive surgery across a body wall and within a body cavity. This is particularly true in abdominal surgery where trocars provide working channels across the abdominal wall to facilitate the use of instruments within the abdominal cavity. Trocar systems may include a cannula, which provides the working channel, and an obturator that is used to place the cannula across a body wall, such as the abdominal wall. The obturator is inserted into the working channel of the cannula and pushed through the body wall with a penetration force of sufficient magnitude to result in penetration of the body wall. Once the cannula has traversed the body wall, the obturator can be removed.

With the cannula in place in the body wall, various instruments, only one at a time, may be inserted through the cannula into the body cavity. One or more cannulas may be used during a procedure. During the procedure, the surgeon manipulates the instruments in different cannulas, sometimes using more than one instrument at a time. Additionally, during laparoscopic procedures, a trocar can be inserted through a body wall and into body cavity through a small opening, incision or puncture. It has been found that the cannula or tube of the trocar must be larger than the instrument to be used within it. It is the goal of laparoscopic surgeons to keep the incision as small as possible. However, the outer diameter of the cannula can largely drives the size of the incision. Efforts are thus made to reduce the wall thickness, the outer diameter, or both of trocar cannulas and thereby reduce the need for large incisions.

Laparoscopic surgery is also well accepted and has evolved to where surgeons are performing complex procedures through fewer and fewer access ports or devices. In some cases complex procedures may be performed through only one access device. It has become evident that a typical access device such as a trocar may not always be the most efficient tool in a crowded laparoscopic surgical environment. For example, trocars may conflict with one another and compete for space in the operative field. In addition, the bulk of a trocar may not be acceptable as it sometimes restricts movement of surgical instruments and shortens the operative length of the instrument by the height of the trocar seal housing. There is also the restriction associated with the tubular construction of the cannula associated with the trocar. These issues can be of additional concern when a surgeon seeks to perform a procedure from a single site where instrument length and mobility can be critical.

SUMMARY

In accordance with various embodiments, a surgical access device providing instrument access into a patient's body is provided. The access device comprises a first support to be positioned externally to a patient's body, a second support to be positioned within a patient's body and a film passageway having a first end connected to the first support and a second end connected to the second support. The film passageway has a non-adjustable length and is disposed through an opening in a patient's body and in direct contact with the opening in the patient's body. The film passageway has a zero or near zero inner diameter due to compressive forces applied by the patient's body in direct contact with the film passageway in absence of an instrument inserted through the film passageway and provides an instrument seal with an instrument inserted through and in direct contact with the film passageway.

In accordance with various embodiments, a surgical access device providing instrument access through an access platform is provided. The surgical access device comprises a first support, a second support and a film passageway. The first support is positioned externally to an access platform in which the access platform comprises a sealing cap removably coupled to a retractor. The second support is removably insertable through an opening in the sealing cap and is positioned under the sealing cap. The film passageway has a first end connected to the first support and a second end connected to the second support and portions of the film passageway are disposed within the opening in the sealing cap and in direct contact with the opening in the sealing cap. The film passageway has a non-adjustable length and provides a zero seal due to compressive forces applied by the sealing cap in direct contact with the film passageway and in absence of an instrument inserted through the first support and the film passageway. In accordance with various embodiments, the film passageway provides an instrument seal against an outer surface of an inserted instrument and an inner surface of the film passageway with the instrument inserted through the first support and the film passageway.

Many of the attendant features of the present invention will be more readily appreciated as the same becomes better understood by reference to the foregoing and following description and considered in connection with the accompanying drawings in which like reference symbols designate like parts throughout.

DETAILED DESCRIPTION

In accordance with various embodiments, a trocar surgical seal or surgical access device is provided that comprises an elongate body or film passageway to be placed through a patient's body or an access platform to thereby provide a working channel for surgical instruments to be inserted into the patient's body for a minimally invasive surgical procedure. In accordance with various embodiments, the film passageway is generally tubular and in various embodiments does not maintain a particular shape. The trocar surgical seal or surgical access device is non-adjustable and/or is collapsible under pressure or radial or circumferential compressive forces exerted by the body wall, surrounding tissue or the material of the access platform. The trocar surgical seal in any configuration or position does not provide resistance or counteract the forces exerted by the body wall, surrounding tissue or the access platform. The trocar surgical seal provides a gas-tight instrument seal against an outer surface of an instrument inserted there through. In various embodiments, the trocar surgical seal also provide a gas-tight zero seal preventing any gas flow out of the patient in the absence of an instrument inserted there through.

The film passageway in various embodiments is between an inner support and an outer support. The inner support secures the film passageway within the patient's body and the outer support is disposed externally and secures the film passageway to the patient's body. The trocar surgical seal is cannula-less, without a seal housing (housing-less) or both and thus among other things eases manufacturing, assembly, packing, storage and operation of the device. The lack of cannula also reduces potential tissue trauma and the incision or opening size required or used. The lack of seal housing also reduces overall surgical space occupied by the device and reduces port crowding.

Figure 1:
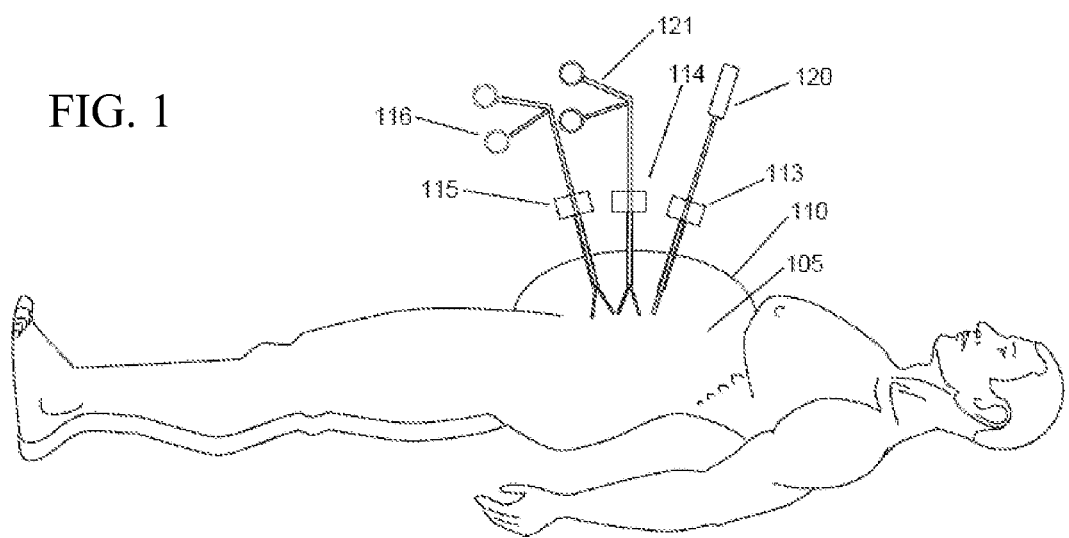
FIG. 1 is a side section view of surgical access devices or trocars used in an exemplary laparoscopic procedure.
Figure 2:
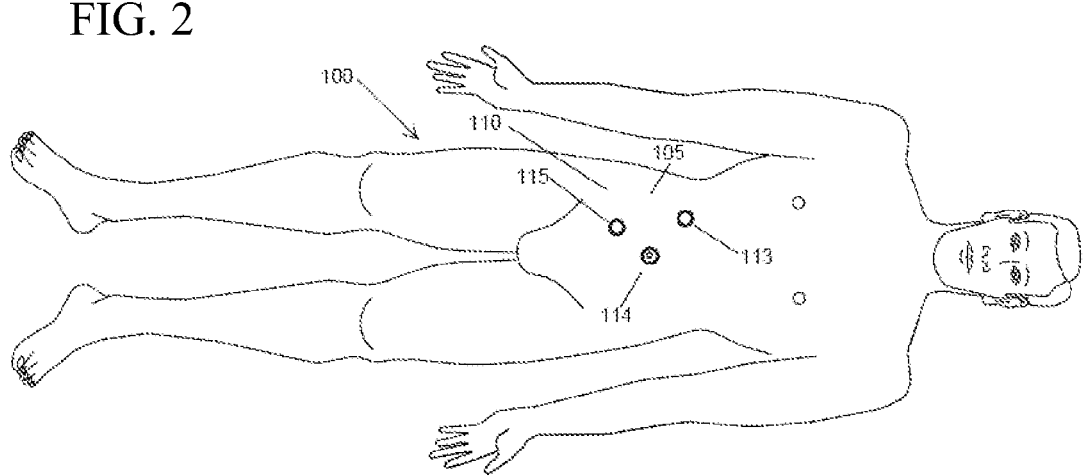
FIG. 2 is a top view of surgical access devices or trocars used in an exemplary laparoscopic procedure.

Referring now to FIGS. 1 and 2, a laparoscopic arrangement is shown where a plurality of access devices or trocars 113, 114, 115 is placed through a body wall 110 and into a body cavity 105 at strategic locations. For most procedures the trocars are placed strategically to provide optimum visualization, access to target areas and maximize the cosmetic result. Laparoscopic instrumentation 116, 120 and 121 are also shown and are not large bore instruments. Many instruments that once required a shaft diameter of 10 mm to 12 mm are provided with a shaft diameter of 5 mm or less. Optical and digital cameras and systems 120 are also provided such as in a 5 mm format.

Figure 3:
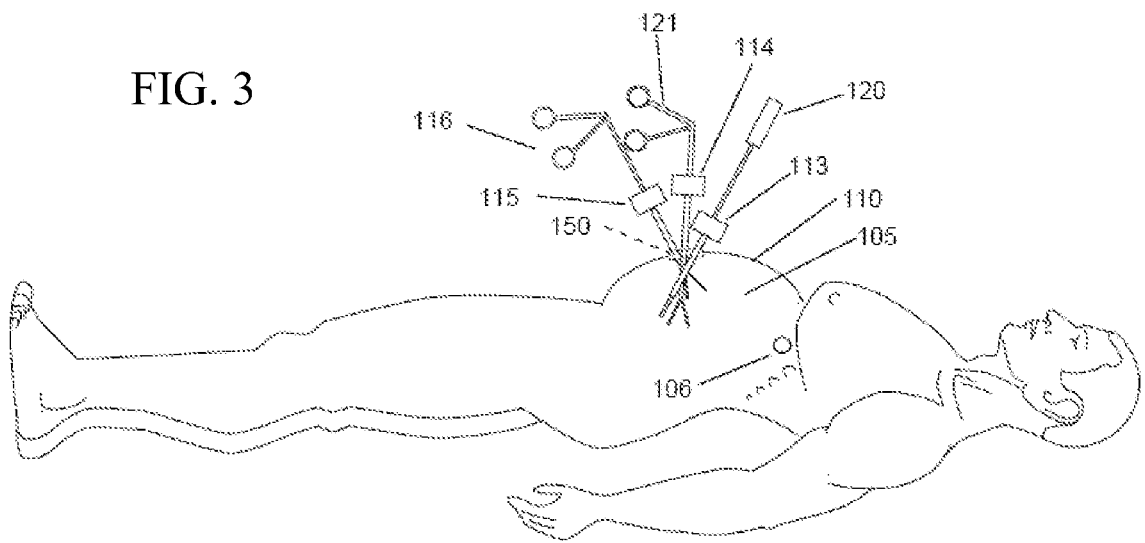
FIG. 3 is a side section view of surgical access devices used in a single-site laparoscopic surgical procedure.
Figure 4:
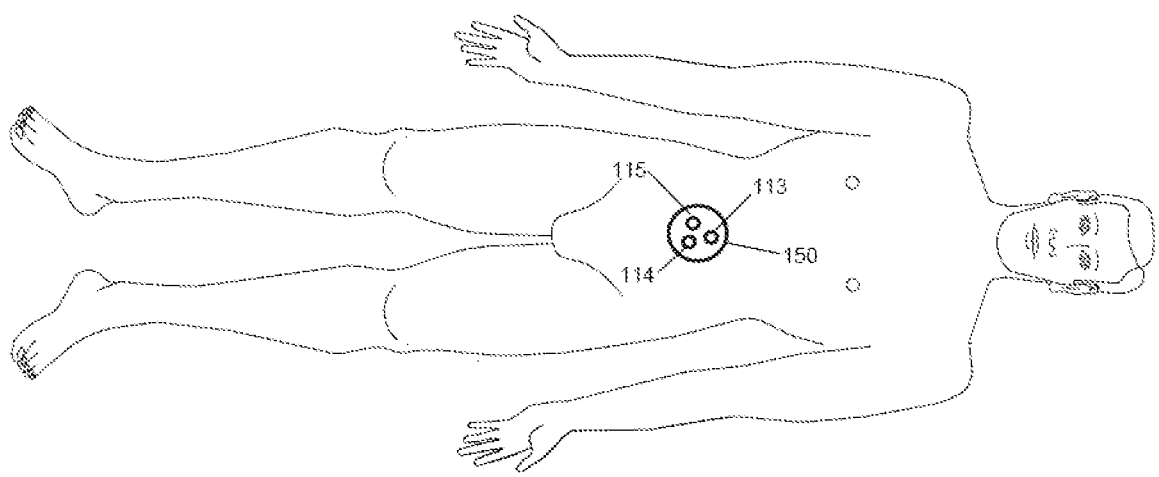
FIG. 4 is a top view of surgical access devices used in a single-site laparoscopic surgical procedure.

Referring to FIGS. 3 and 4, a laparoscopic procedure such as a single-site laparoscopic surgery is shown where trocars 113, 114 and 115 are arranged very close together. It can be seen that rigid trocars having a rigid cannula and a large seal-housing may present concerns where they are used close to each other. In addition, the length of the instruments 116, 120 and 121 may be challenging when using specific length trocars due to for example that the target area 106 may be oblique to the single-site entry 150.

Figure 5:
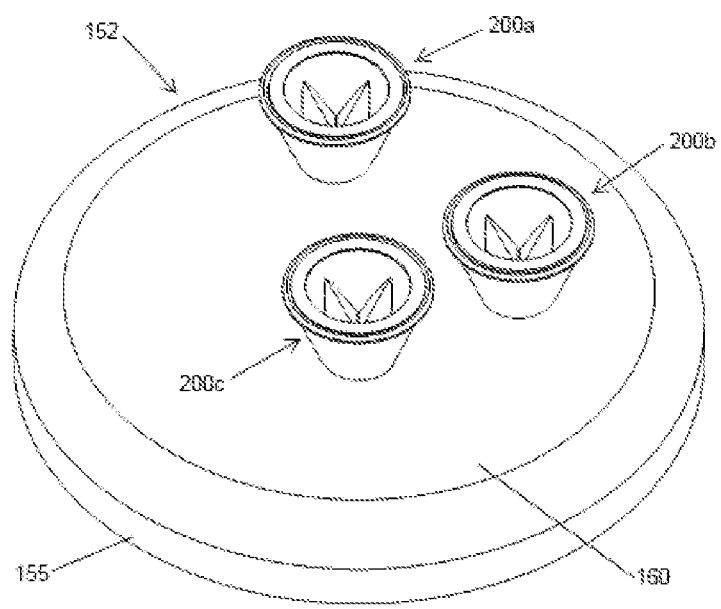
FIG. 5 is an oblique view of a trocar surgical seal or surgical access device and an access platform in accordance with various embodiments.
Figure 6:
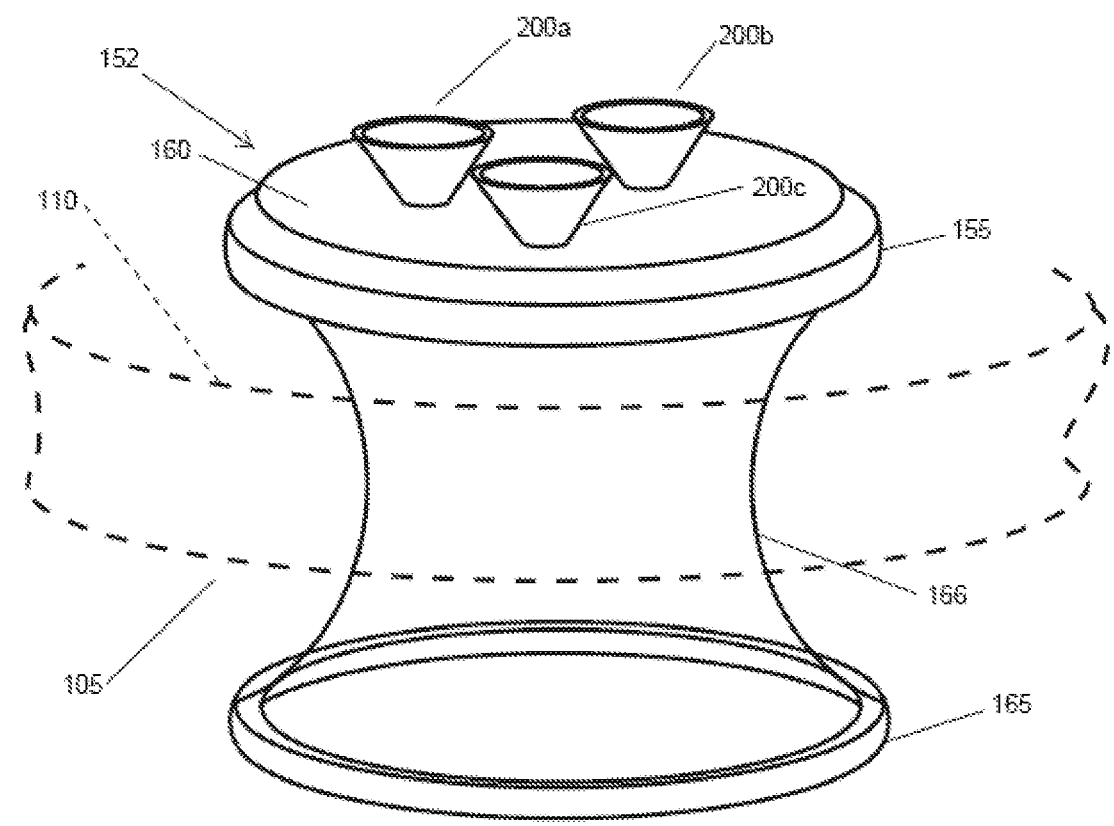
FIG. 6 is a perspective view of a trocar surgical seal and an access platform in accordance with various embodiments.
Figure 7:
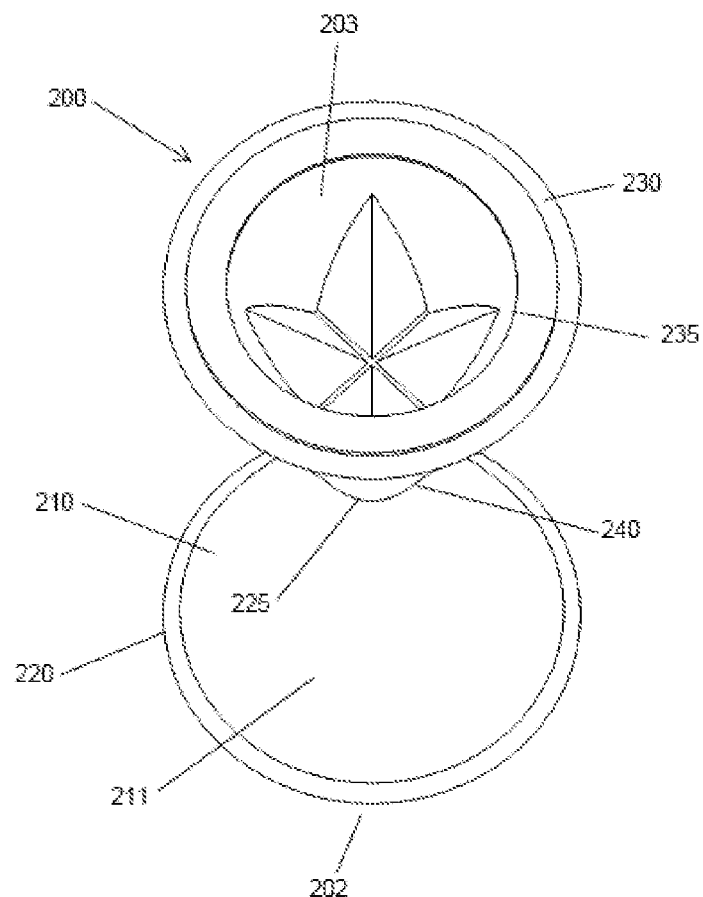
FIG. 7 is an oblique view of a trocar surgical seal in accordance with various embodiments.
Figure 8:
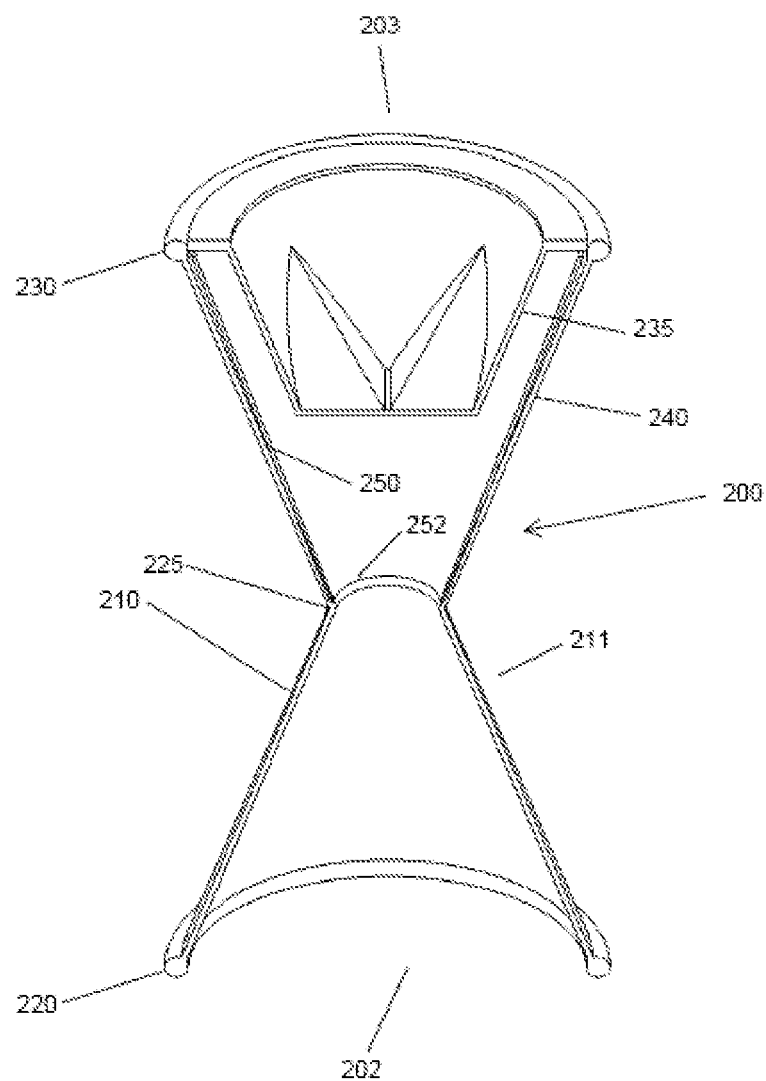
FIG. 8 is side section view of a trocar surgical seal in accordance with various embodiments.
Figure 9:
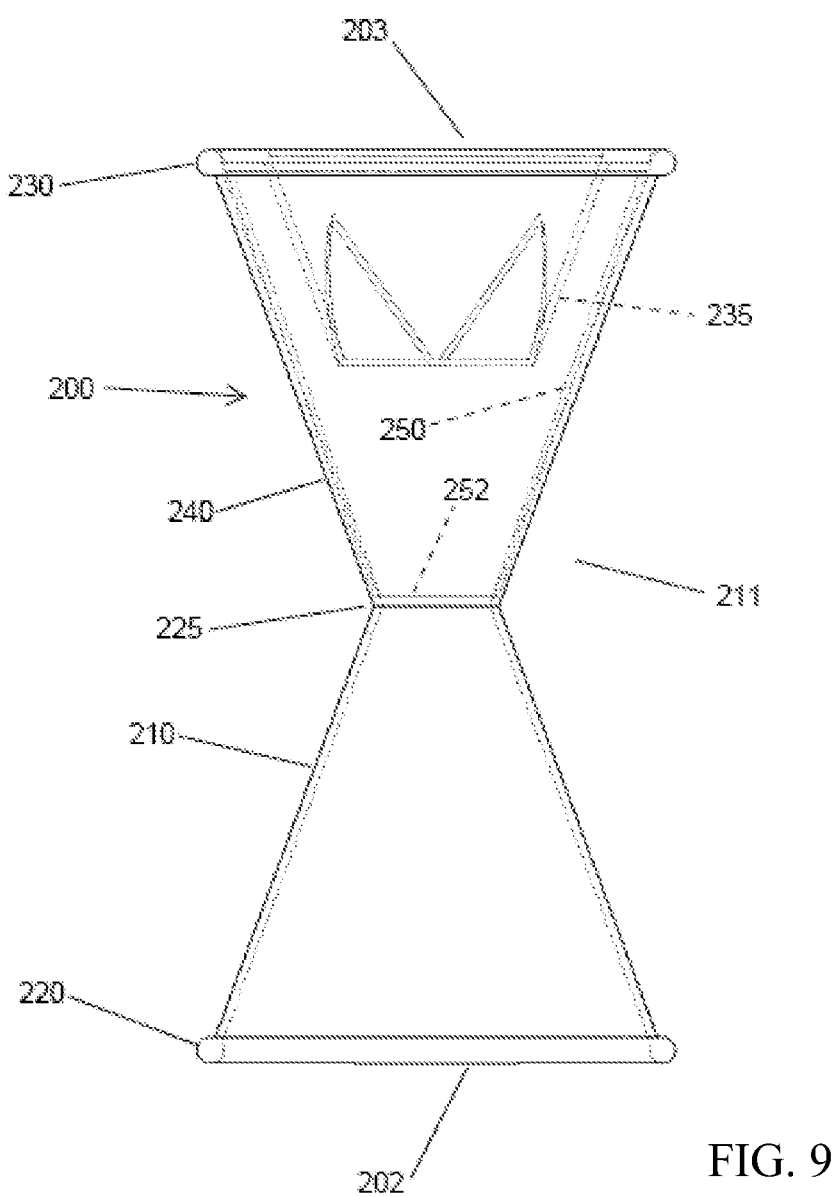
FIG. 9 is an oblique view of a trocar surgical seal in accordance with various embodiments.
Figure 10:
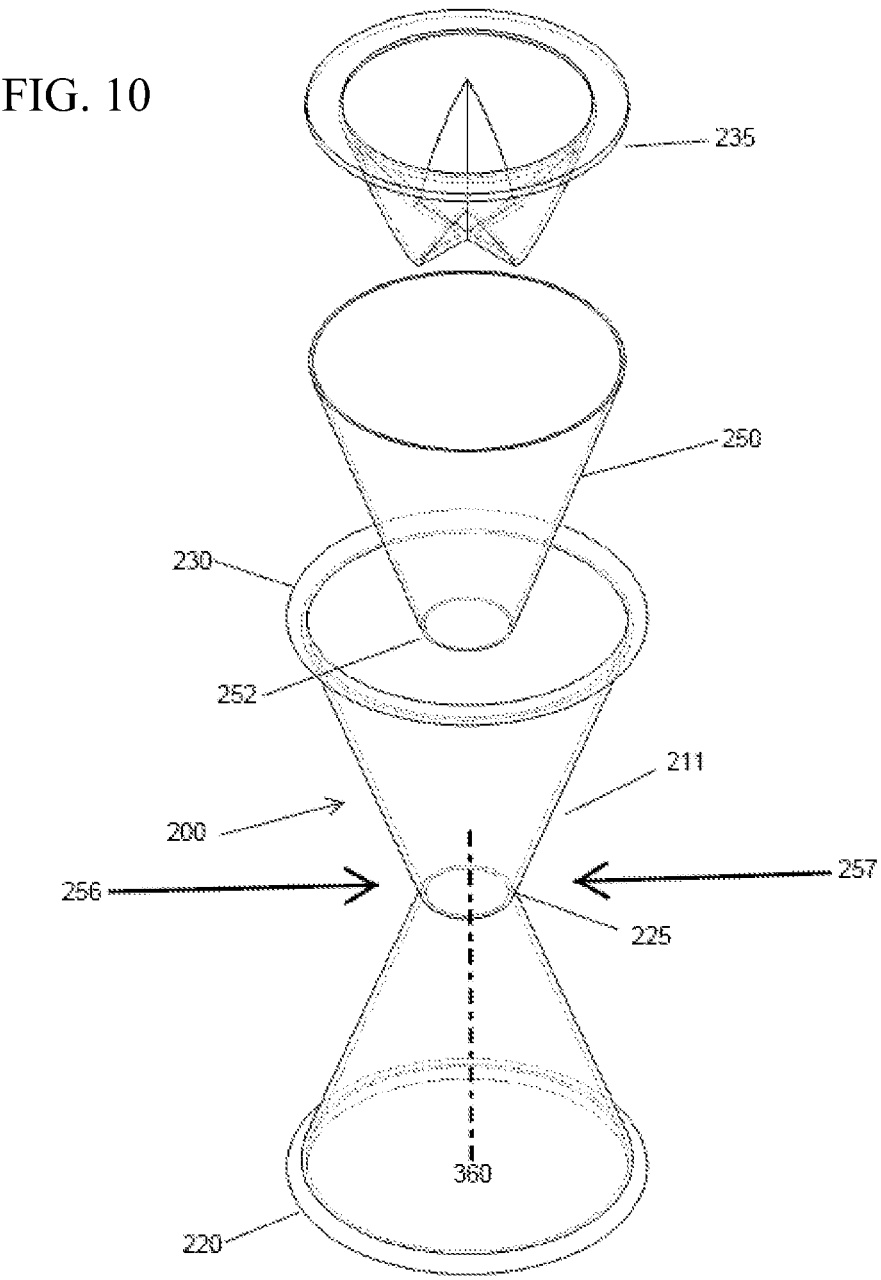
FIG. 10 is an exploded view of a trocar surgical seal in accordance with various embodiments.
Figure 11:
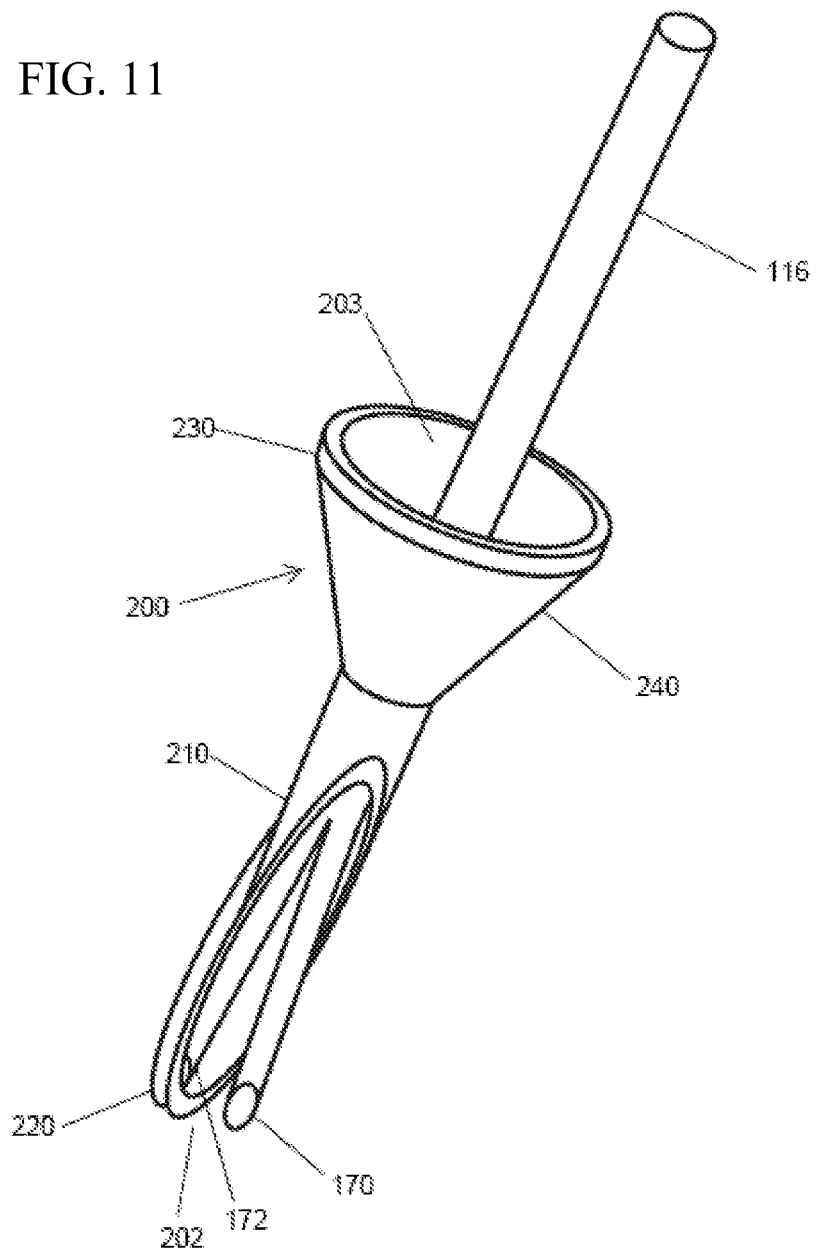
FIG. 11 shows a grasper and a trocar surgical seal in accordance with various embodiments.
Figure 12:
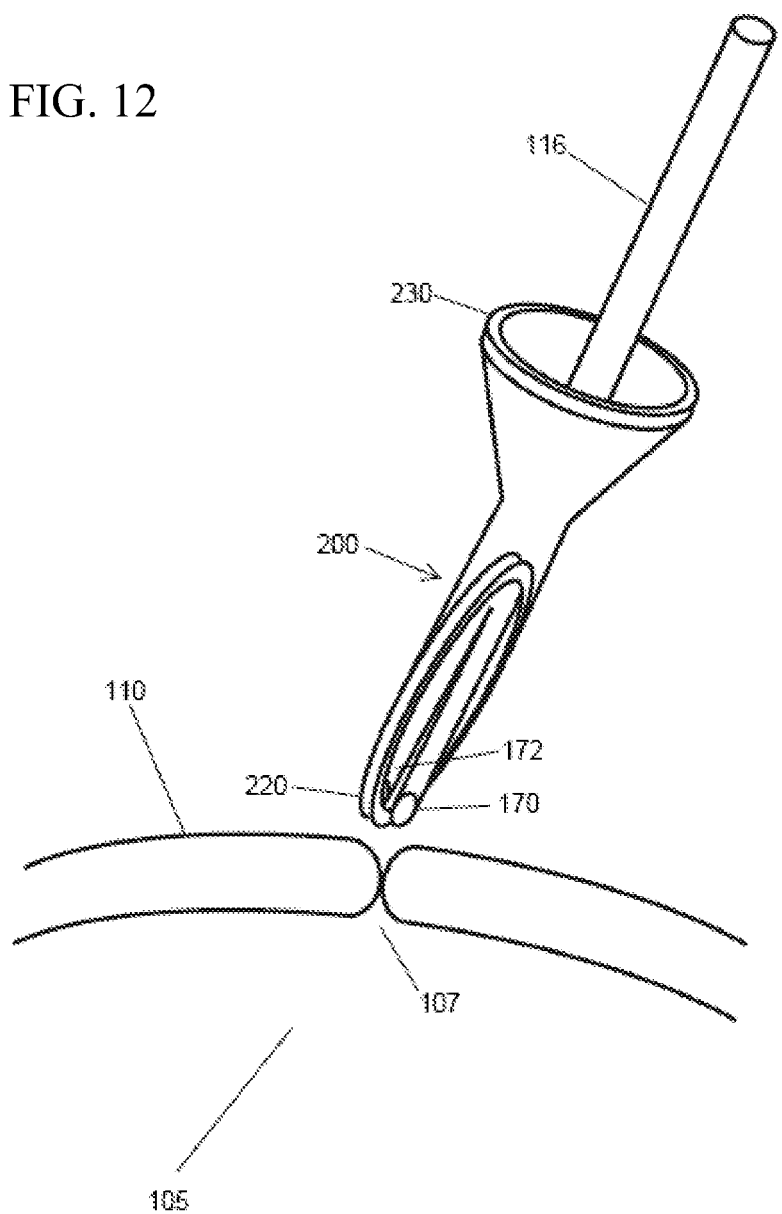
FIG. 12 shows a trocar surgical seal in accordance with various embodiments being placed.
Figure 13:
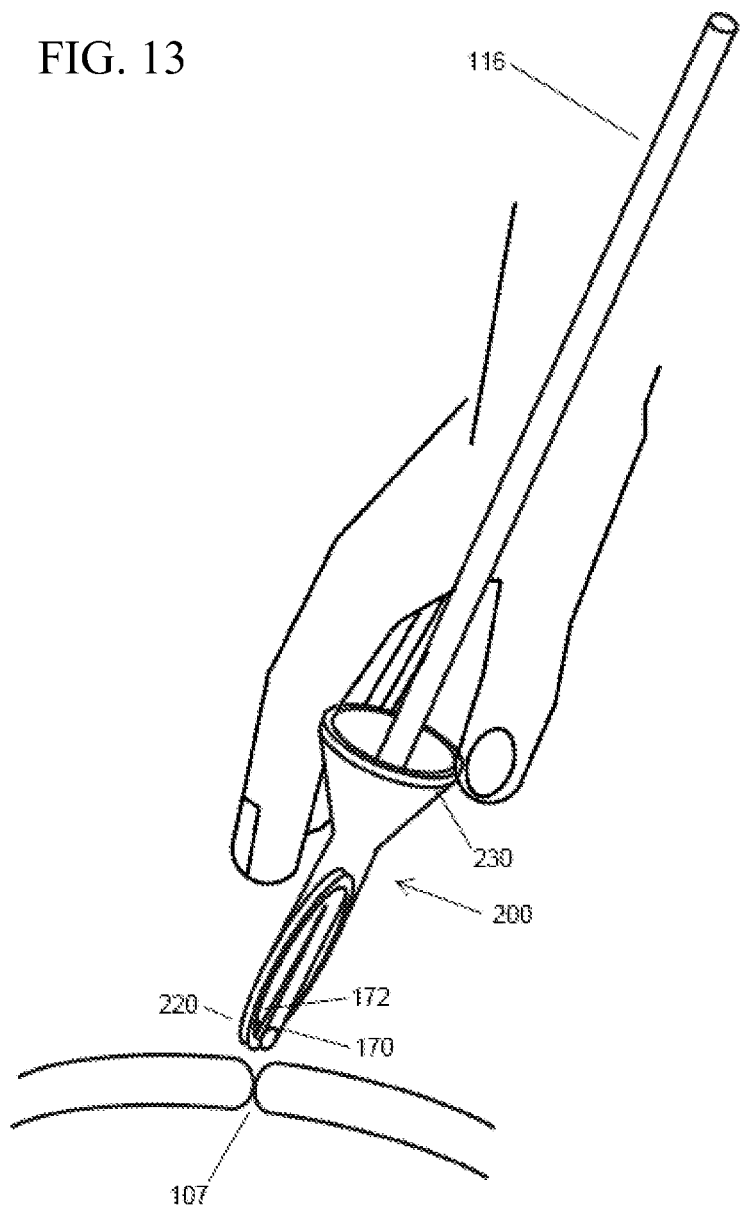
FIG. 13 illustrates a placement of a trocar surgical seal in accordance with various embodiments.

With reference to FIGS. 5 and 6 a surgical access system in accordance with various embodiments of the present invention is provided. In various embodiments, an access platform 152 is shown having a sealing cap that includes a support ring 155 surrounding a penetrable self-sealing seal 160. In various embodiments, the support ring 155 is disposed within the body wall or externally and in various embodiments a tension-able and elongate tube or membrane is affixed or removably coupled to the support ring 155. In various embodiments, an inner support ring 165 is coupled to the tube or membrane 166 and is disposed within the patient. The access platform in one embodiment allows a surgeon to perform a surgical procedure through a single incision or opening. A plurality of trocar surgical seals or surgical access devices 200a, 200b, 200c in accordance with various embodiments of the present invention may be placed through the penetrable seal 160 and thereby provide access into the body cavity 105. The small diameter and very low profile of the access ports or devices 200a, 200b, 200c allow inserted instruments to be manipulated freely. Also, the low profile and lack of a seal-housing and cannula, bulky, rigid or otherwise, allow the instruments to be inserted further into the body cavity and into hard-to-reach areas.

In accordance with various embodiments, the penetrable seal 160 comprises a gel material, low durometer elastomer, foam, or various combinations thereof and in one embodiment trocar surgical seals may be inserted there through. In one embodiment, the penetrable seal or the gel material includes a triblock or diblock copolymer and in one embodiment also includes oil. In one embodiment, the gel material is coupled to or molded onto the support ring. In one embodiment, the sealing cap is removably coupled to a protector or retractor and in various embodiments the support ring includes a cavity, connector, lever, or any combination thereof, to removably attach the sealing cap to an outer portion or a ring of the retractor. In one embodiment, the retractor is adjustable and configured to roll a sheath around the outer ring that is releasably attachable to the support ring. In one embodiment, the penetrable seal or gel material includes one or more instrument seals, zero seals, or combinations thereof and in one embodiment the surgical access devices may be inserted there through.

Referring now to FIGS. 7-10, a trocar surgical seal or surgical access device 200, e.g., trocar surgical seals 200a, 200b and 200c, in accordance with various embodiments of the present invention is shown comprising a generally "hour-glass" shaped elongate body or film passageway 211 having an open proximal end 203, an open distal end 202 and a narrowed waist 225. The body 211 appears as a double-ended funnel 210, 240 having the narrow ends connected. The proximal 203 and distal 202 ends of the body 211 in one embodiment are supplied with enlarged, flexible support rings or first and second supports 220, 230 that may be elongated as required. The proximal funnel portion 240 in one embodiment may also include or be fitted with a rigid or semi-rigid matching funnel liner or shield 250. Additionally, in accordance with various embodiments, the proximal end 203, the distal end 202 or both may include or be fitted with a zero seal 235 to prevent retro-flow of insufflation gas or fluids. In one embodiment, the zero seal 235 is a double-duckbilled elastomeric seal sized and configured to prevent gas from leaking or escaping, e.g., from flowing from the distal end 202 and out the proximal end 203.

The hour-glass shaped body 211 in one embodiment is constructed from an elastomeric material such as silicone, polyurethane or various rubbers. The narrow waist portion 225 is sized and configured to seal around a range of laparoscopic instruments inserted through the access device. The elastomeric material or material of the film passageway is configured to provide a seal with minimal surface contact with the inserted instrument within the working channel 360 of the trocar surgical seal 200. The tissue or material surrounding the hour-glass seal body 211 exerts a compressive influence 256, 257 upon the seal body 211 to assist in perfecting the instrument seal within the working channel 360. The compressive influence 256, 257 may provide a zero seal and thus no zero seal 235 may be required to prevent gas flow when there is no instrument within the working channel 360 of the access device 200. In accordance with various embodiments, the body or film passageway is used without the rigid or semi-rigid shield 250 or the zero seal 235. Therefore, in accordance with various embodiments, the assembly of an elongate body 211, a rigid or semi-rigid shield 250 and a zero seal 235 can be separable for use in any combination. Additionally, in one embodiment, the zero seal can be removed for specific or operational uses such as removal of tissue or specimens from within a body cavity. In accordance with various embodiments, the film passageway 211 is made of a material different from the zero seal 235 and the shield 250 and/or, in one embodiment, the shield is made of a material that is different from the film passageway 211 and the zero seal 235.

The rigid or semi-rigid shield 250 in accordance with various embodiments may be constructed of specifically selected material. For instance, polyethylene, polypropylene or nylon may be selected for use when friction upon an inserted instrument is to be reduced or minimized. The distal opening 252 in accordance with various embodiments may be sized and configured to minimize instrument contact with the elongate body or film passageway material and minimize frictional drag upon an instrument within the working channel 360. The distal opening 252 is sized and configured to reduce potential instances where a sharp or pointed instrument could puncture or tear the elongate body 211. The sized distal opening 252 also serves to move the elongate body's orifice or waist portion along with the movement of the inserted instrument so that the orifice is not elongated when an instrument is moved drastically off-axis or obliquely within the working channel 360. In accordance with various embodiments, if the surgeon requires an instrument to be inserted or placed in an extremely oblique position within the working channel 360, the zero seal 235 and the shield 250 may be removed from within the elongate body 211 along the shaft of the inserted instrument and then subsequently replaced if desired after movement of the instrument is completed.

FIGS. 11-14 in accordance with various embodiments of the present invention illustrate a method for placing the trocar surgical seal or surgical access device 200, 300, 380 through a body wall 110 and into a body cavity 105 or through an access platform 152. A laparoscopic grasper 116 may be inserted through the proximal end 203 of the trocar surgical seal 200 and advanced to a point where the jaws 170, 172 of the grasper 116 may clamp upon the distal support ring 220 of the access device. Tension may be placed between the distal support ring 220 and the proximal support ring 230 thereby elongating the distal support ring 220. The elongated support ring is subsequently inserted through an incision or purposeful defect/opening 107.

Figure 14:
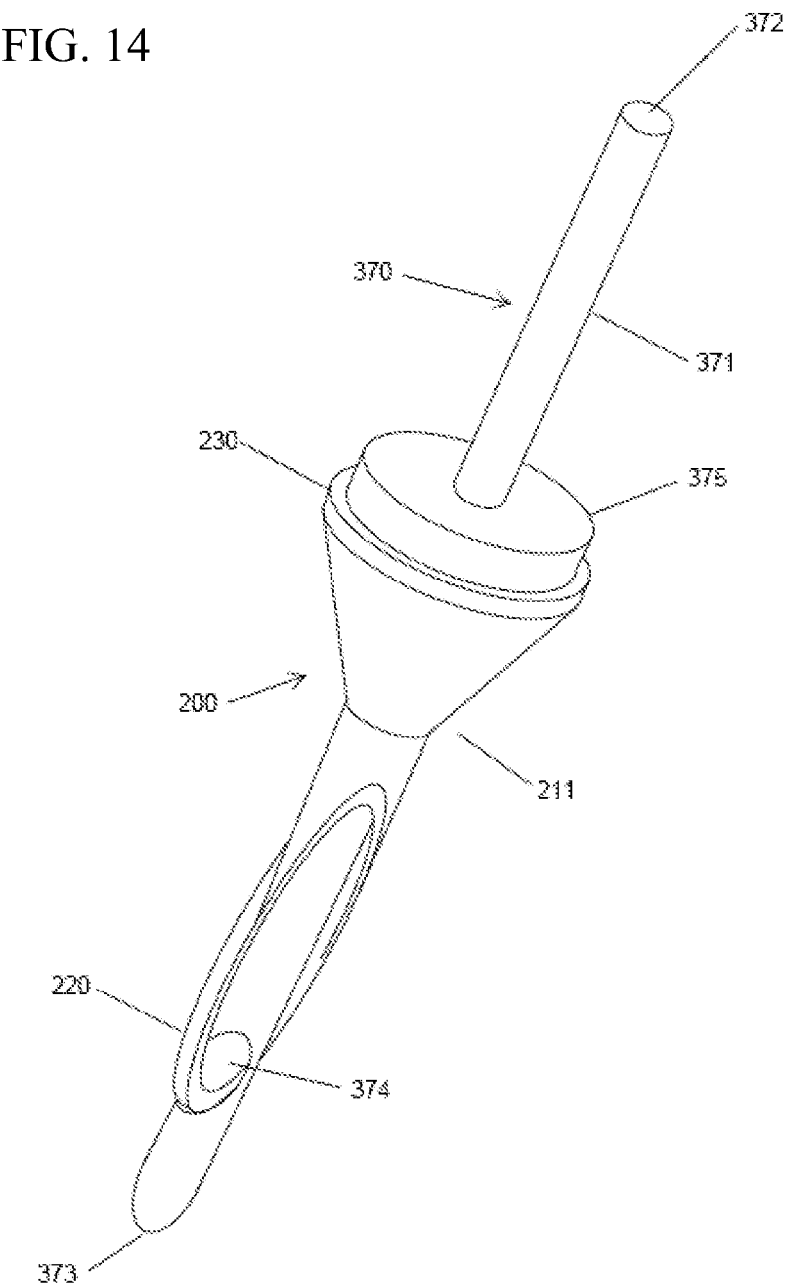
FIG. 14 is a perspective view of a placement or insertion tool and a trocar surgical seal in accordance with various embodiments.

In accordance with various embodiments, an insertion method is illustrated in FIG. 14 and may comprise an obturator or obturator insertion device 370 having a proximal end 372, a distal end 373 and an elongate body 371. The proximal end 372 comprises a handle (not shown) sized and configured to allow a surgeon to provide a pushing force to the obturator 370. The elongate body 371 transfers the pushing force to the distal end 373 of the obturator 370. The distal end 373 of the obturator 370 in accordance with various embodiments may have a tip 273, be pointed or configured to provide penetration through tissue or platform material. In one embodiment, the distal end 373 of the obturator 370 may have, at least, one, first holder 374 that engages the distal ring 220 of the access device 200. The obturator 370 in accordance with various embodiments has a second or proximal holder 375 that is sized and configured to engage the proximal ring 230 of the access device 200 so as to tension the body 211 between the holder 374, 375 and to reduce the profile of the distal ring 220 for insertion through a body wall or access platform.

Figure 15:
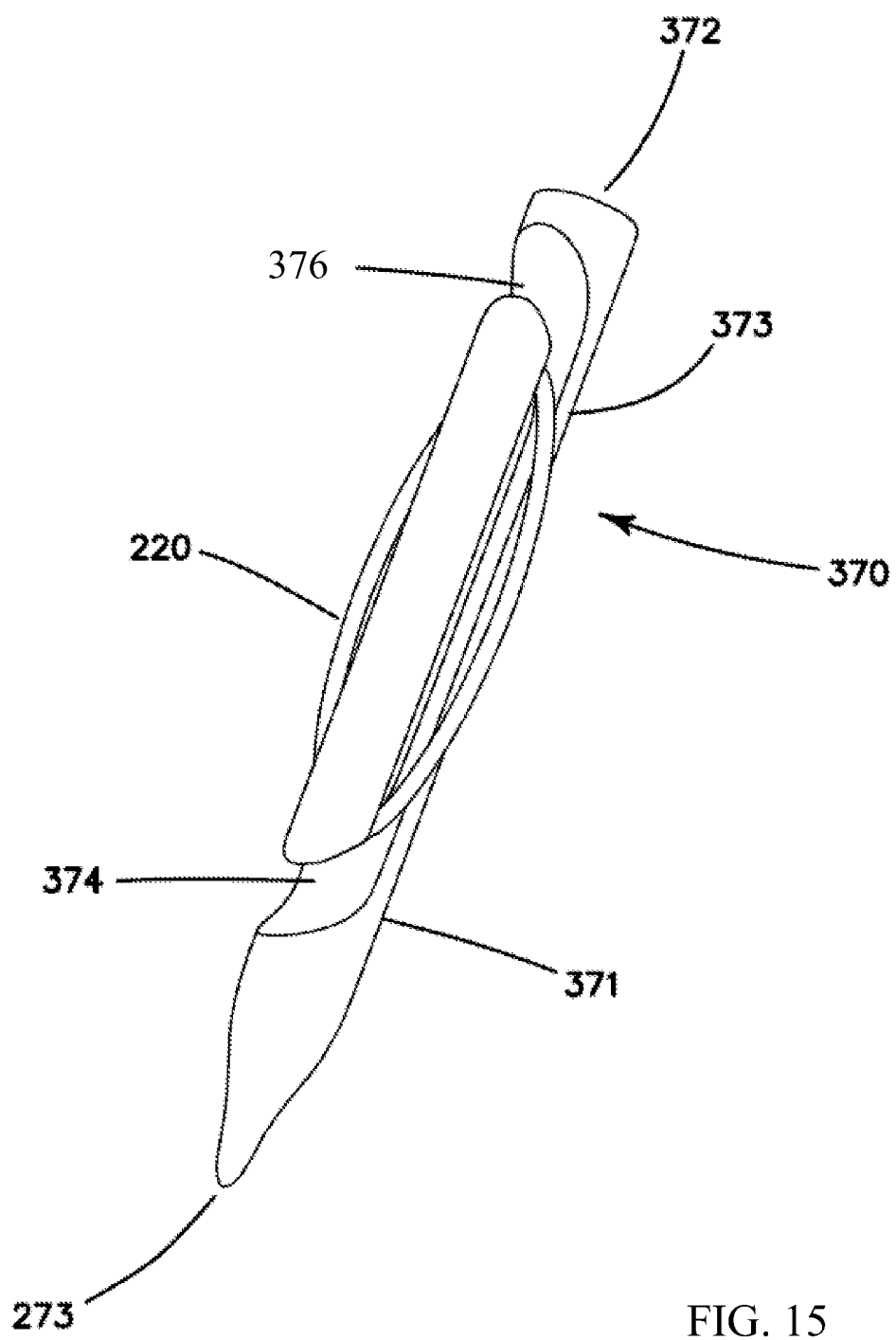
FIG. 15 is a perspective view of a portion of a placement or insertion tool for use with a trocar surgical seal in accordance with various embodiments.

Referring to FIG. 15, the distal portion 373 of an insertion device 370 is shown comprising at least one engaging feature or hook 374 that is sized and configured to retain the distal retention ring 220 or distal end associated with the trocar surgical seal 380 in accordance with various embodiments of the present invention. As illustrated, the distal retention ring 220 may be stretched to a low insertion profile by tensioning the ring 220 against the hook or distal retainer 374. After insertion, the tension may be relaxed and the distal ring 220 released from the distal retainer 374. In accordance with various embodiments, a second, proximal retainer 376 is included on the insertion device 370. The distal retention ring 220 of the access device 380 may be tensioned between the distal retainer 374 and the proximal retainer 376 for insertion of the access device through a body wall. The insertion device in one embodiment comprises a handle and elongate shaft 371 along with a point or tip 273 to facilitate insertion of the insertion device through the body wall with no or minimal tissue trauma. In one embodiment, the tip 273 is configured to separate tissue and in various embodiments is bladeless or lacks sharp or cutting edges or surfaces. In various embodiments, the tip is transparent or configured to provide only visual access there through by, for example, a laparoscope and in various embodiments, the tip is transparent or configured to provide visual access therethrough along with insufflation or evacuation access. In various embodiments, the tip or portions of the shaft includes a vent, aperture or configured to provide only insufflation or evacuation access. The transparent, bladeless and/or insufflation tip assists in accordance with various embodiments in which the trocar surgical seal is inserted into a body cavity that is not insufflated or under pneumoperitoneum pressure. In one embodiment, the distal retainer 374, the proximal retainer 376 or both can be disengaged or slid open to release the distal support 220 after insertion through the body wall or access platform.

Figure 16:
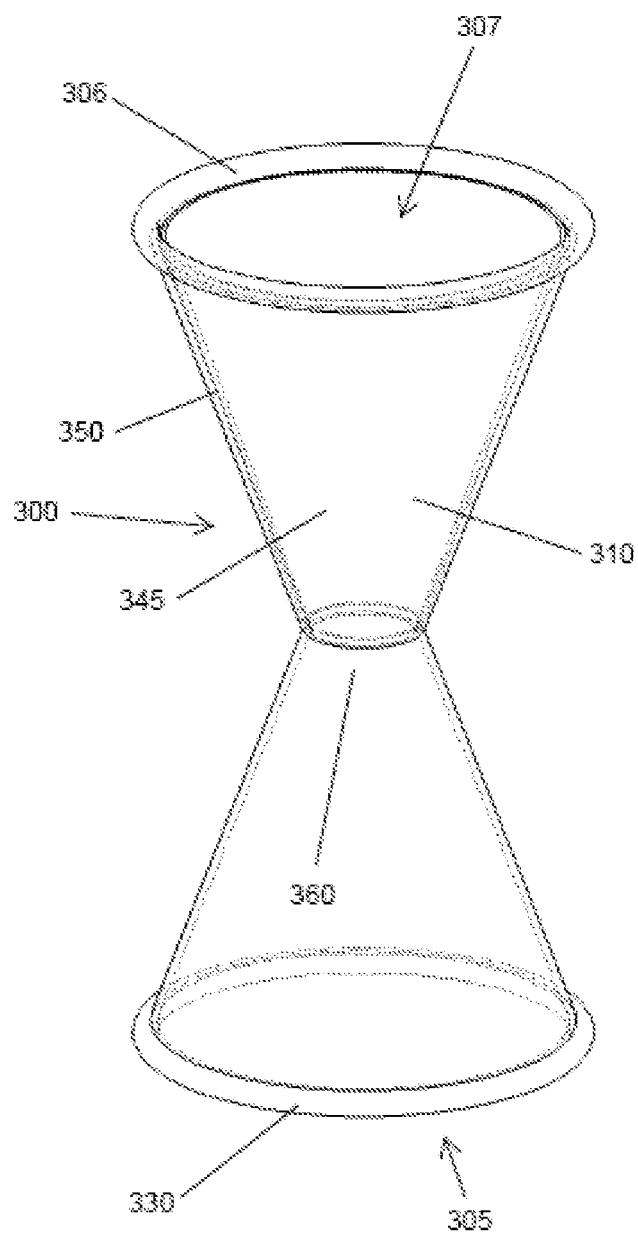
FIG. 16 is a side oblique view of a trocar surgical seal or surgical access device in accordance with various embodiments.
Figure 17:
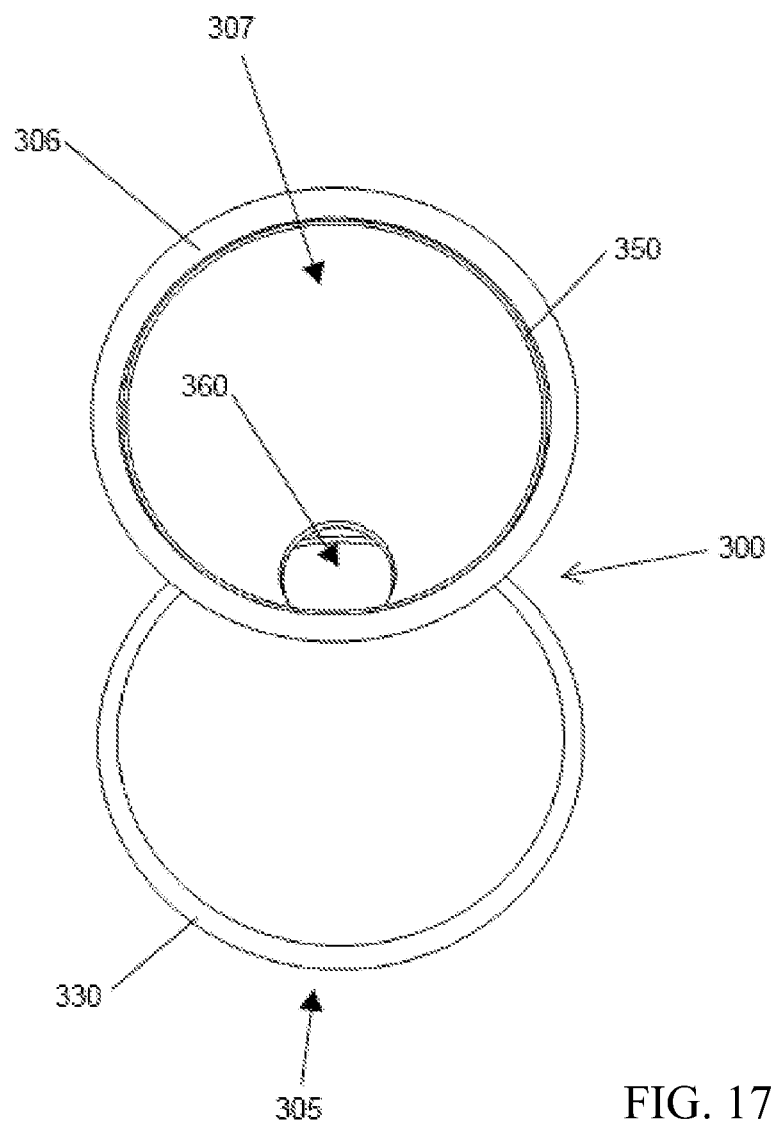
FIG. 17 is a top oblique view of a trocar surgical seal in accordance with various embodiments.

With reference to FIGS. 16 and 17, a trocar surgical seal 300 is provided in accordance with various embodiments of the present invention. The trocar surgical seal or access device comprises an hour-glass shape constructed from a tubular woven or braided sleeve 310. The woven or braided sleeve may be thermally set to provide the hour-glass shape. A flexible distal support ring 330 may be associated with a distal end 305 of the woven or braided sleeve and a rigid or flexible proximal support ring 306 may be associated with the opposite proximal end 307 of the woven or braided sleeve. The woven or braided hour-glass sleeve in one embodiment may be coated or impregnated with an elastomeric material to form a substantially gas-tight access device. In one embodiment, a rigid or semi-rigid conical shield 350 may be placed within the proximal hour-glass portion 345 of the woven or braided sleeve to provide protection from pointed or sharp inserted instruments within the working channel 360 of the access device 300. If required for complete closure when no instrument is within the working channel 360, a zero seal may be associated with the proximal open end 307, the distal end 305 or both ends of the braided or woven access device 300.

Figure 18:
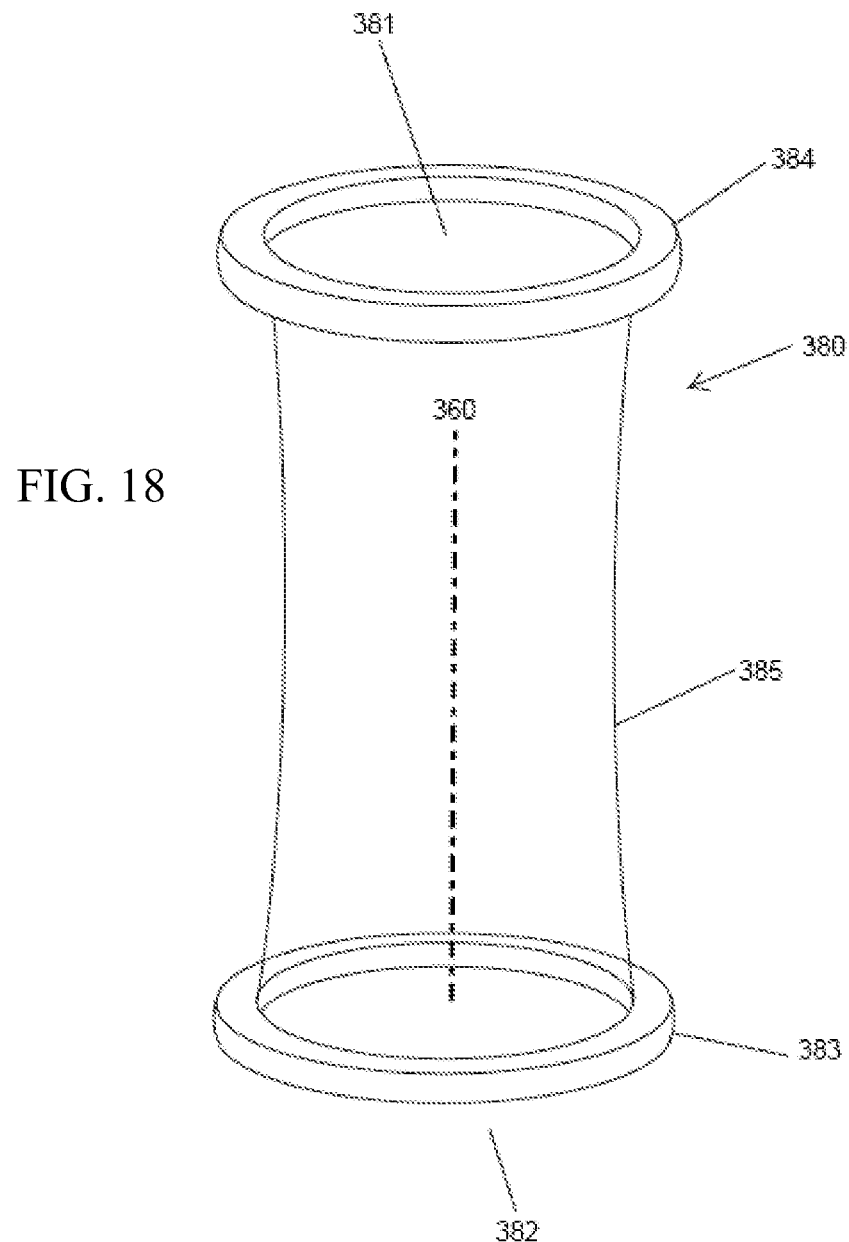
FIG. 18 is a side view of a trocar surgical seal or surgical access device in accordance with various embodiments.
Figure 19:
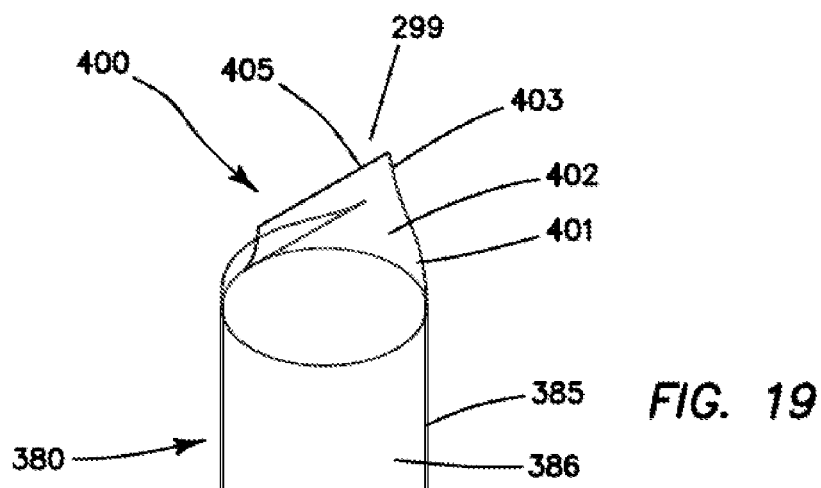
FIG. 19 is a perspective view of a trocar surgical seal or surgical access device with a formed end in accordance with various embodiments.
Figure 20:
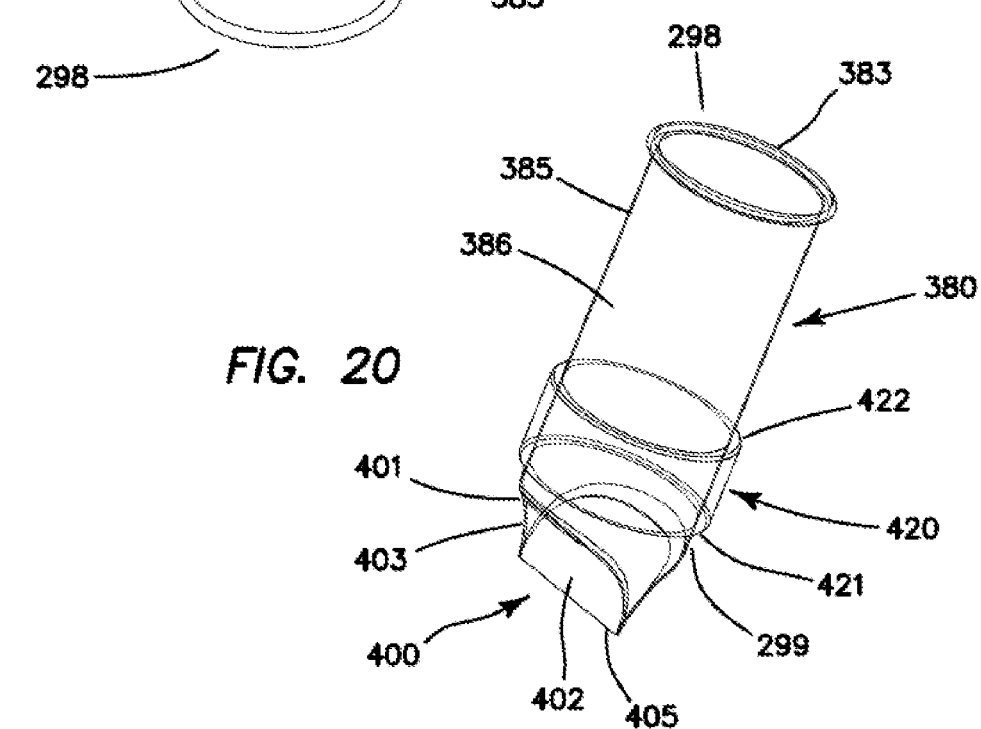
FIG. 20 is a perspective view of a trocar surgical seal or surgical access device with a bolster in accordance with various embodiments.
Figure 21:
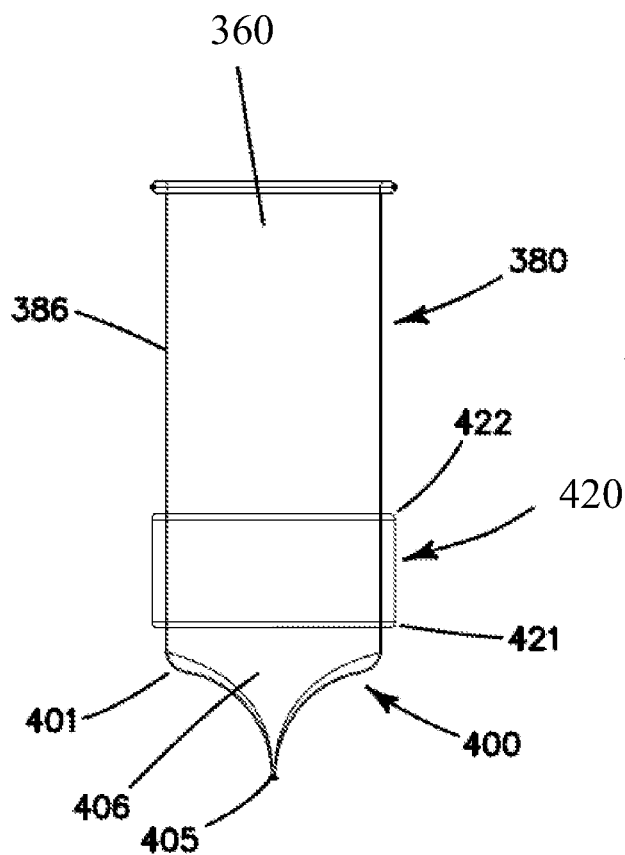
FIG. 21 is a side section view of a trocar surgical seal or surgical access device with a bolster in accordance with various embodiments.
Figure 22:
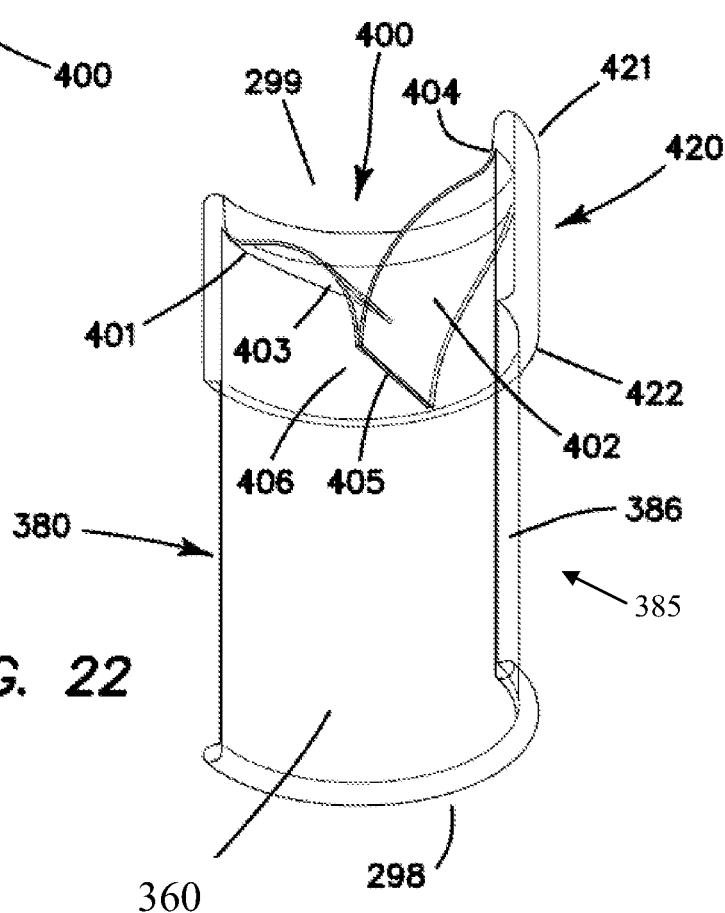
FIG. 22 is a section view of a trocar surgical seal or surgical access device with a bolster and an invaginated portion in accordance with various embodiments.
Figure 23:
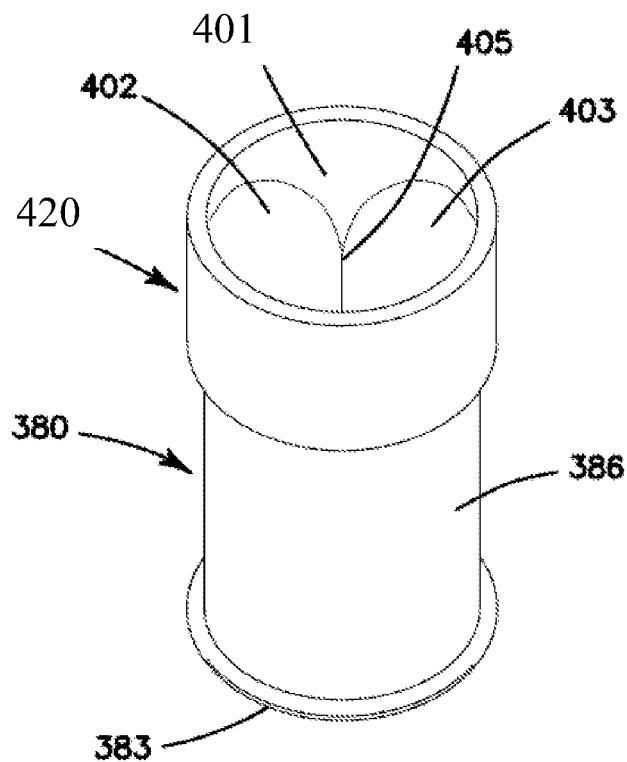
FIG. 23 is a perspective view of trocar surgical seal with a bolster in accordance with various embodiments.
Figure 24:
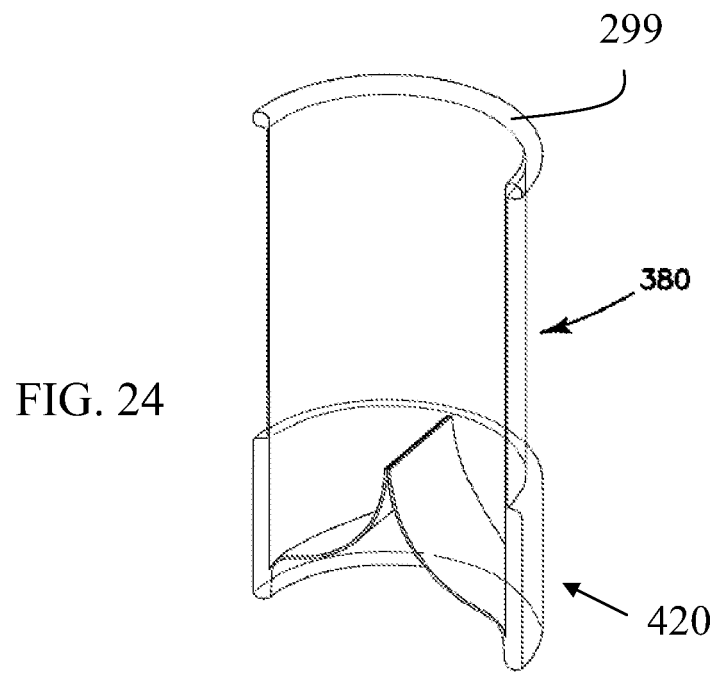
FIG. 24 is a section view of a trocar surgical seal with a bolster in accordance with various embodiments.

With reference to FIG. 18, a trocar surgical seal 380 is provided in accordance with various embodiments of the present invention. The trocar surgical seal or access device 380 includes an elongate tube or film passageway 385 with a proximal end 381 and a distal end 382. The distal end 382 in one embodiment may include a flexible support ring 383 that may be deformed to allow positioning through a body wall or an access platform. The proximal end 381 of the tube 385 in one embodiment may be fitted with a rigid or flexible support ring 384 and in accordance with various embodiments will remain outside a body wall or seal platform. The tube 385 extends between the rings 383 and 384 and may be compressed by the tissue or access platform material through which the tube extends. In one embodiment, a rigid or semi-rigid conical shield may be placed within the film passageway 385 to provide protection from pointed or sharp inserted instruments within the working channel 360 of the access device 300. If required for complete closure when no instrument is within the working channel 360, a zero seal may be associated with the proximal end 381, the distal end 382 or both ends of the film passageway.

In accordance with various embodiments, the trocar surgical seal includes a braid, fabric or woven sleeve 310 or a portion thereof integrated into a film passageway 211, 385, both of which are configured to extend through the body wall or access platform. The braid provides a low-friction, expandable lead-in. The braid serves to prevent direct contact between the body wall and the inserted instrument which can occur in the absence of the film when the tissue extrudes through interstitial spaces of the braid. By preventing direct contact between the body wall or tissue and an inserted instrument, the frictional forces associated with advancement and withdrawals of an instrument are reduced. In accordance with various embodiments, the film passageway prevents direct contact between the body wall and the braid serves to maintain the integrity or protection of the opening in the body wall during insertion, advancement, and withdrawal of a surgical instrument.

In one embodiment, as a surgical instrument is inserted into the trocar surgical seal or access device, the braid expands to the size, e.g., the width or diameter, of the inserted instrument and directs the instrument through the trocar surgical seal. The film passageway 211, 385 can be formed from relatively distensible or relatively non-distensible film materials including polyolefin, polyurethane, polyethylene, polypropylene, nylon, and polyester. As an instrument is inserted into the braid, the braid expands while the body wall or surrounding body tissue resists expansion. As such, the body wall or surrounding body tissue forces or applies a compressive radial or circumferential load or force against the surgical seal to sealingly engage the outside diameter of an inserted instrument while eliminating direct frictional contact between the inserted instrument and the tissue.

In accordance with various embodiments, the film passageway 211, 385 can be formed of a thin material with a thickness that is in the range of 0.0005" to 0.002". The braid in accordance with various embodiments is expandable and can accommodate a large range of instrumentation sizes which can range from 3.5 mm to 16 mm in diameter. The braid and the film passageway of the surgical seal 200, 300, 380 eliminate or reduce the potential for an instrument to tear or catch the trocar surgical seal if the instrument is inserted off-center or off-axis with respect to the longitudinal axis of the surgical access device or the body opening.

In one embodiment, bifurcated instruments can damage the trocar surgical seals especially if they are inserted or removed off-center or off-axis. The braid and film passageway combinations serve to direct the instrument through the aperture of the surgical seal. The braid and the film work to expand the aperture of the trocar surgical seal in response to the insertion of an instrument. This expansion action of the braid and the film passageway enables the diameter of the surgical seal aperture to be minimized. The minimized diameter of the trocar surgical seal's aperture allows the surgical seal to sealingly engage a large range of inserted instruments. With other access devices, it can be challenging to minimize the diameter of an instrument seal's aperture and also avoid puncture in response to the insertion of bifurcated instruments such as clip appliers.

The braid and the film passageway 211, 385 of the trocar surgical seal also serve to reduce the force required to insert and advance an instrument through the surgical seal. The coefficient of kinetic friction (f) for the braid/film verses a metal or polymer instrument shaft is significantly less than that for an elastomeric seal verses a metal or polymer instrument shaft. The coefficient of kinetic friction values range from 0.15 to 0.5 for polymers such as polyester verses steel, whereas the coefficient of kinetic friction values for elastomers versus steel range from 1.6 to 10. The braid in combination with the film passageway eliminates direct contact between the shaft of an inserted instrument and the tissue and therefore minimizes the frictional forces required to insert and advance an instrument through the trocar surgical seal.

The film passageway 211, 385 in one embodiment is a 0.0005" polyolefin film. In one embodiment, the braid is woven from a 0.001" diameter polyester monofilament is positioned adjacent to or bonded or embedded to the film passageway. The braid in one embodiment is flared at its proximal end, distal end or both to enable ease of insertion and withdrawal of instruments. In one embodiment, a ring, such as a polyethylene ring, is bonded to the distal ends of the braid and/or film passageway to prevent inversion or migration during instrument withdrawal. In accordance with various embodiments, instruments include laparoscopic and endoscopic instruments, probes, scopes, trocars, cannulas and other surgical access devices or instruments.

The braid in accordance with various embodiments is made from natural or synthetic monofilament thread materials. For example, the braid may be made from polyester, Kevlar, carbon fiber, Gore-Tex (expanded PTFE), Nomex, Nylon, fiber glass, cotton, polypropylene, and ceramic. The braid, film passageway or both in accordance with various embodiments are made from a hygroscopic or superabsorbent polymer monofilament material. As such, the braid, film passageway or both can absorb fluids transferred from inserted or withdrawn instruments to prevent fluids from subsequently transferring from the access device to an inserted instrument such as a laparoscope to prevent reduction in visualization through the laparoscope.

The braid in accordance with various embodiments is permanently coated or treated to reduce friction between inserted or withdrawn instruments and the braid. For example, the coating or treatment of the braid include hydrophilic polymer coatings, Teflon (PTFE) coatings, cyanoacrylate coatings, Parylene coatings, plasma surface treatments, and chlorination treatments. The braid and film passageway in accordance with various embodiments are mechanically locked in place by including an additional ring that would trap the proximal ends of the braid and film passageway between the ring.

In accordance with various embodiments of the present invention, the trocar surgical seal or access devices 200, 300, 380 do not have a predefined shape and accommodate an elongate surgical instrument inserted therein. The access device may be generally tubular if held from the proximal or distal end and with gravity acting thereon. The shape of the access device 200, 300, 380 is defined by compressive forces exerted on the access device by for example a body wall. The access device extends from or near the outside of the body cavity and distally towards the inside of the body cavity. The shape of the access device is also defined by instrument inserted into the working channel of the access device. As such, in accordance with various embodiments, unlike other trocars or surgical access devices, the access device 200, 300, 380 is collapsible or does not exert a radial or expansive force against the body wall or opening in the patient. Hence, the access device does not force an opening or attempt to maintain a predefined opening or shape, e.g., a tubular shape of a cannula or retractor. The access device thus minimizes potential tissue trauma and reduces incision or opening size. Also, in accordance with various embodiments of the present invention, the access device 200, 300, 380 has open and unobstructed proximal and distal ends. As such, a seal housing is not present, used or attachable to the proximal or distal end of the access device thereby minimizing surgical space occupied by the access device and preventing port crowding. Accordingly, in various embodiments, the trocar surgical seal 200, 300, 380 lacks or is without a seal housing, a cannula and/or a retractor and is in direct contact with the body wall or opening in the patient or access platform.

In accordance with various embodiments of the present invention, the trocar surgical seal or access devices 200, 300, 380 having a generally tubular, hour-glass or various other shapes are sized and configured to accommodate an elongate surgical instrument inserted therein. In various embodiments, the body or film passageway 211, 385 of the access devices has at a first open end. In various embodiments, the first open end includes a first support and in various embodiments the first support includes a compliant ring, a proximal or external bolster or collar and a seal sized and configured to prevent flow of gas in one direction. The body of the access devices in accordance with various embodiments includes a compliant ring at a second open end. The body or film passageway 211, 385 of the access device in various embodiments is constructed from a very thin, durable, elastomeric material or a very thin non-elastomeric material that is easily compressed by the tissue of the body wall through which it has been inserted. Elastomeric materials may include silicone, polyurethane, latex, poly-isoprene and the like. Non-elastomeric may include material such as polyolefin, polyester, polyethylene or the like.

In accordance with various embodiments of the present invention, the trocar surgical seal or access devices 200, 300, 380 may be introduced through a body wall and into a body cavity through an incision or opening that is considerably smaller than the incision required by a typical access device or trocar. For instance, a trocar that accommodates 5 mm instruments requires an incision that accommodates a 7 mm cannula or tube. The outer diameter of the cannula or tube is responsible for the larger incision size. The access device 200, 300, 380 for example comprises a body constructed of a film material having a wall thickness of 0.003"-0.005". The nearly negligible wall thickness allows for an incision size that is substantially smaller than that required by traditional trocars. In accordance with various embodiments of the present invention the incision size could be smaller than the designated size of the instrument indicated for use. For example, an incision, through which a 5 mm instrument is to be used, may be reduced to approximately 3 mm. The inserted instrument will temporarily dilate or enlarge the tissue defect and perfect a gas-tight seal between the body wall, film passageway and the instrument. The small incision or opening size is useful as a small incision imposes a compressive, circumferential sealing load upon an inserted instrument; results in less scarring of subject tissue; generally requires no mechanical closure such as stitches or staples; and is less likely to become hernia site than a larger incision.

In accordance with various embodiments, the film passageway 211, 385 is made of material, e.g., polyolefin, and/or has a thickness, e.g., between 0.0005 to 0.002 inches, that is not able to extend in a longitudinal direction or resists extension or forces to stretch the material in a longitudinal direction. In accordance with various embodiments, the film passageway 211, 385 is made of material and/or has a thickness that is not able to extend or resists extension or forces to stretch the material in a horizontal direction or a direction traverse to the longitudinal direction except as it is urged to unfold under the influence of an inserted instrument within the film passageway.

In accordance with various embodiments of the present invention, the body or film passageway of the access device 200, 300, 380 may be constructed by welding thin sheet-film into a tube or may be blow molded or otherwise formed into a generally tubular shape. In one embodiment, an irradiated ultra-thin-walled, cross-linked polyolefin tube that may be post-formed into a desired shape or condition by the application of heat to all, or a portion of the tubular member is used. This manufacturing process may also facilitate attachment of the tubular structure to proximal and distal supports or rings without the use of adhesives. In various embodiments, the film 211, 385 includes various slip agents such as waxes, soaps, diatomaceous earth, silicone oils, and fluoropolymers to reduce the drag force on inserted instruments.

With reference to FIGS. 19-24 in accordance with various embodiments of the present invention a trocar surgical seal or access device 380 is provided. The access device 380 has a distal end 298, a proximal end 299 and an elongate body or film passageway 385 extending between the distal end 298 and proximal end 299. The film passageway 385 comprises an elongate mid section 386. A distal end of the elongate mid section 386 in one embodiment supports or includes a "ring-shaped" retainer or support 383. In accordance with various embodiments, the material from which the elongate mid section 386 extends and curves along a peripheral portion 401 into tapers, folds or curved surfaces 402, 403 meeting at a slit 405 and thereby forming a zero seal 400.

In various embodiments, the proximal end of the elongate mid section 386 supports or includes a bolster or ring 420. In accordance with various embodiments, the material of the elongate mid section 386 extends through the bolster 420 in a proximal direction and subsequently extends distally to a peripheral portion 401 into curved surfaces 402, 403 and meeting at slit 405 to form the zero seal 400. The bolster 420 stabilizes the seal and the mid section relative to each other and the patient's body or access platform. The bolster 420 in one embodiment has a proximal portion 421 and a distal portion 422 in which the height or distance between the portions is about a third of the height of the mid section to assist in stabilizing the seal relative to mid section, the patient's body, the access platform or instruments inserted therein. The bolster 420 also in one embodiment provides a stable structure to form or attach the seal or to maintain the zero seal under insufflation pressure. As such, in one embodiment, the area or cavity 406 adjacent to the seal 400 and the working channel 360 remains sealed in the absence of an inserted instrument.

In accordance with various embodiments, the material of the elongate mid section 386 extends through the bolster 420 proximally and is subsequently invaginated distally to form a self-closing or zero seal 400 in the presence of pressure gradients within the cavity 406 and lumen or working channel 360 of the access device between the distal end of the elongate mid section 386 and the proximal end of the elongate mid section 386 or along an inner surface or portion of the seal. The self-closing seal 400 comprises inverted, invaginated portions 402, 403 that are formed by returning the proximally extending mid section portion to within the lumen 360 of the elongate mid section 386. The invaginated portion is configured to exhibit a substantially planar cross-section resembling a "duck-billed" seal. In one embodiment, pneumoperitoneum pressure further maintains or assists in the maintenance of the film portions 402, 403 in a sealed condition in the absence of an inserted instrument. In accordance with various embodiments, the seal 400 is similarly formed in addition to or only at the distal end 298. In accordance with various embodiments, the bolster 420 is thicker, wider, and higher and/or is made of a material that is more rigid, thicker or both than the first support, the second support, the film passageway or any combination thereof. In various embodiments, the bolster is made of a material that is different from the first support, the second support, the film passageway or any combination thereof.

Figure 25:
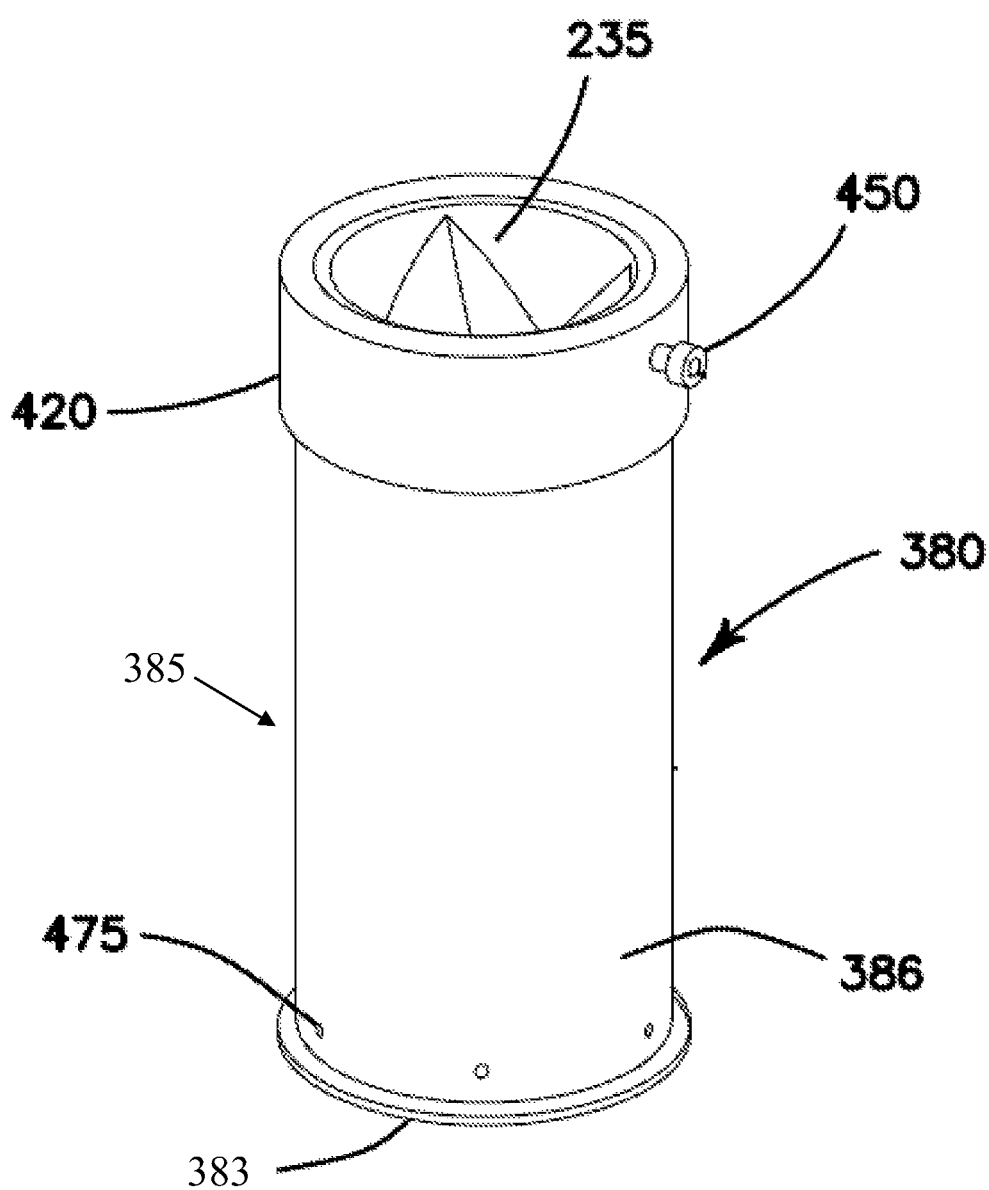
FIG. 25 is a perspective view of a trocar surgical seal or surgical access device having a fluid port in accordance with various embodiments.
Figure 26:
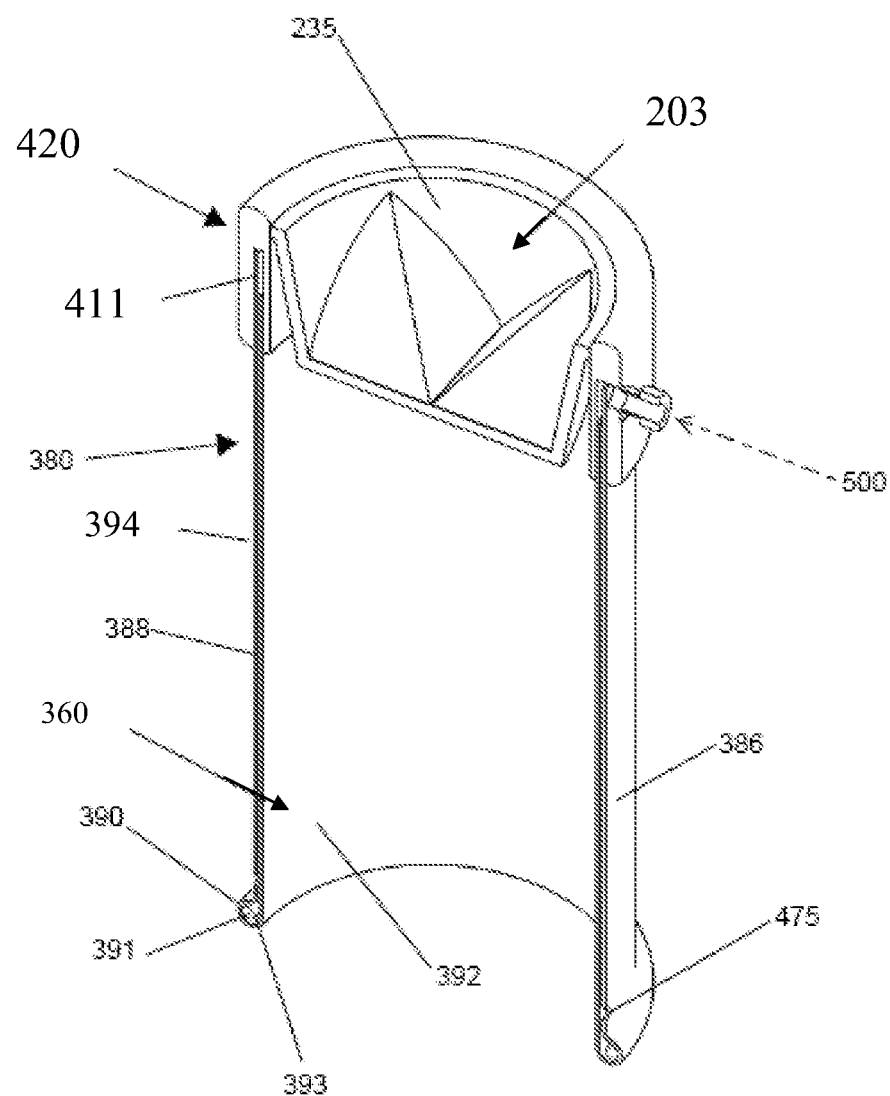
FIG. 26 is a perspective section view of a trocar surgical seal having a fluid port in accordance with various embodiments.
Figure 27:
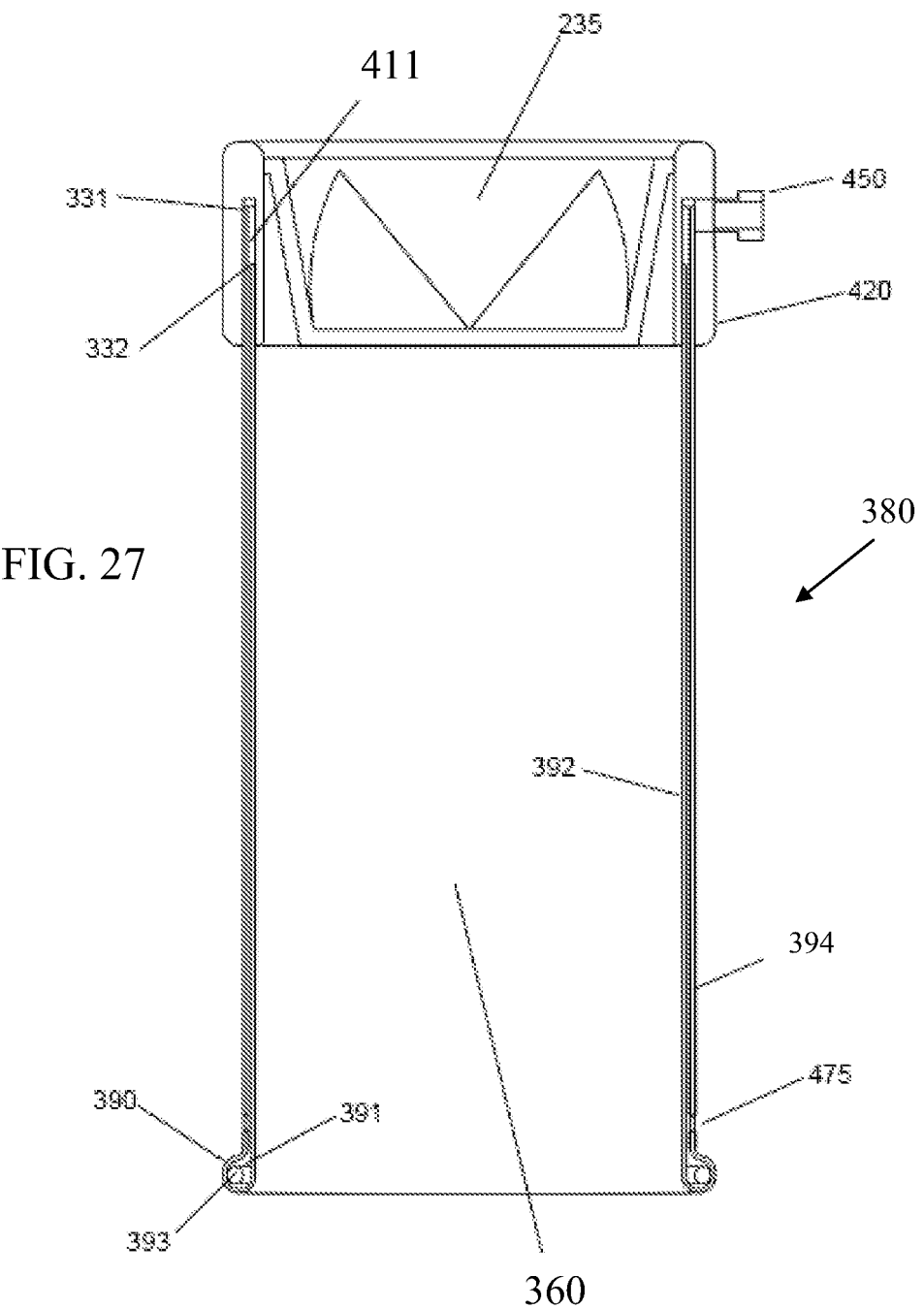
FIG. 27 is a side section view of a trocar surgical seal having a fluid port in accordance with various embodiments.

Referring now to FIGS. 25-27, a trocar surgical seal or access device 380 in accordance with various embodiments comprises a film passageway 211, 385 that comprises a double-walled, concentric structure where a tubular body is inverted upon itself so that a first end 331 of the body adjoins a second end 332 of the body. A ring shaped support 393 in one embodiment may be inserted into the space 391 between the walls 392, 394 and urged into the formed distal pocket 390 where the film is folded. The two adjoining ends 331, 332 are subsequently attached to a bolster 420 in accordance with various embodiments.

In various embodiments, near the distal end of the inverted sleeve body, one or more holes or openings 475 may be formed in the outer wall 394. The one or more holes are smaller in diameter than the working channel 360 or lumen through the film passageway. A fluid connector 450 in one embodiment may be connected to the external bolster 420 that communicates with the distal openings 475 in the outer wall 394 of the access device 380 through a space or channel 388 between the walls 392, 394 of the inverted sleeve body or an opening or channel 411 between the bolster 420 and the walls 392, 394. Gas or fluid may thus be administered or removed through the access device, for example, by connecting a gas supply 500 to the fluid connector 450 of the bolster 420 and allowing gas to flow between the walls 392, 394 and through the distal openings 475 in the outer wall 394 of the access device 380. In one embodiment, a gas or fluid passageway is provided to/from the fluid connector 450 directly through the bolster or the film passageway and into the working channel, e.g., between the zero seal and the film passageway. The gas pressure within the trocar surgical seal and between the coaxial walls can provide additional sealing capability to the trocar surgical seal 380 between the penetrated tissue and an inserted instrument within the working channel 360 of the access device 380. The trocar surgical seal also remains un-housed and in direct contact with the body wall.

Figure 28:
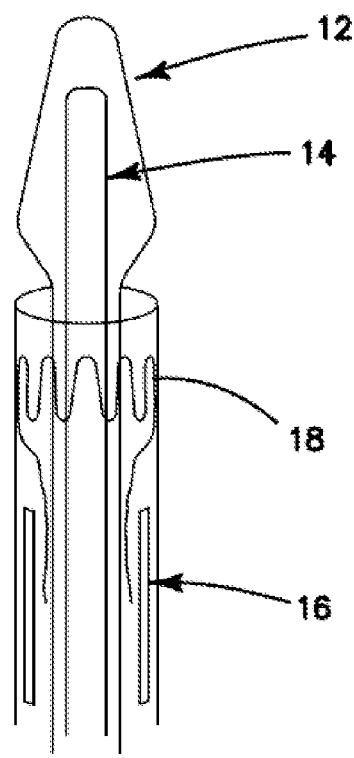
FIGS. 28-29 illustrate an insertion device and a trocar surgical seal or surgical access device in accordance with various embodiments.
Figure 29:
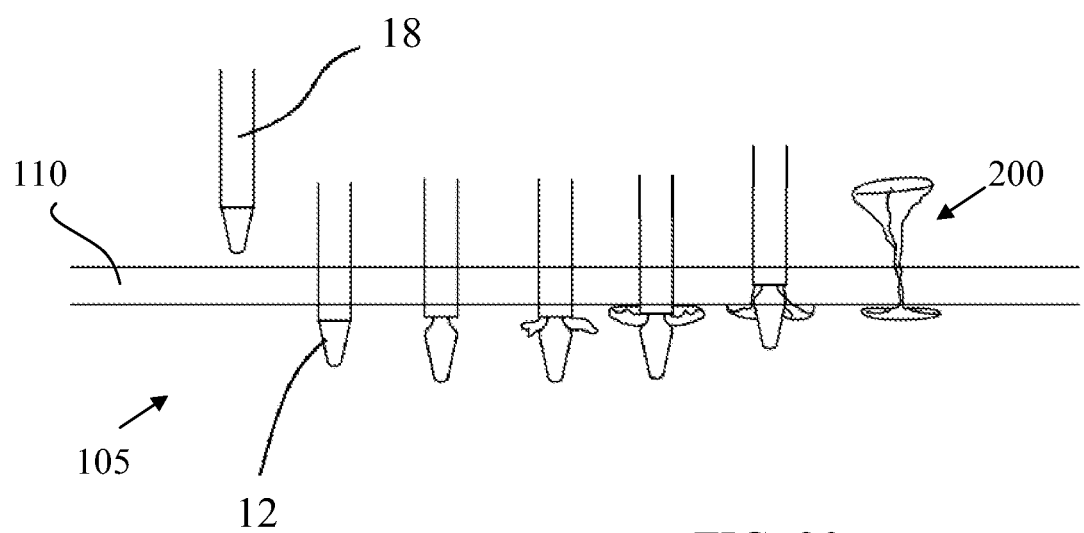

In FIGS. 28 and 29, an insertion device in accordance with various embodiments is shown. The insertion device includes an obturator 12 and in one embodiment includes an optical viewing channel 14 to ensure proper placement of the trocar surgical seal within a patient's body or access platform. The support or distal portion of the access device is shown disposed near the distal end of the insertion tube 18 with a movable deployment slide 16 to eject the trocar surgical seal out of the tube and into the patient. FIG. 29 further illustrates exemplary steps or stages of an insertion of the trocar surgical seal in accordance with various embodiments of the present invention starting with the trocar surgical seal outside the patient's body and within an insertion or deployment device and ending with the trocar surgical seal deployed and disposed through the patient's body.

In accordance with various embodiments described throughout, the trocar surgical seal 200, 300, 380 is capable of accommodating irregularly shaped instruments or objects and in various embodiments is a nearly friction-free, self-sealing, utilizing a small incision or opening and having a low-profile but allowing the use of full-sized laparoscopic instruments. In accordance with various embodiments, a trocar surgical seal 200, 300, 380 is provided and in various embodiments has a body or film passageway with an open and unobstructed lumen there through and unobstructed and open ends. The film passageway 211, 385 in various embodiments is radially collapsible or compressible under radial or circumferential force exerted by a body wall or surrounding body tissue and thus does not maintain a particular shape, e.g., tubular. In one embodiment, the film passageway 211, 385 can be flatten or compressible or collapsible longitudinally and/or radially to assist in packing or storing of the access device. A first support and a second support are provided on each respective ends of the film passageway in accordance with various embodiments. In accordance with various embodiments, movement of the first or second supports or the film passageway relative to each other provides insufficient force to enlarge the inner diameter of the film passageway or to retract the opening in the patient's body or the access platform. Retraction of the body wall prevents an instrument or zero seal from forming or causes the seal to leak.

The second support is to be disposed internally relative to the patient's body and may be constructed of a flexible material so that the support may be deformed for insertion through a body wall or an access platform. The second support may be shaped or compressed by a tensioning or insertion device to provide a low profile insertion shape. The second support in various embodiments is circular and has structural stability to maintain a circular shape in use. In various embodiments, the second support is connected to a second, open end of the film passageway. In one embodiment, the first and second supports have the same inner and/or outer diameters and/or are made of the same material.

The film passageway 211, 385 in various embodiments is a formed as a tube that is constructed of a durable but flexible material having a thin wall thickness. In various embodiments, the film passageway 211, 385 is made of polyethylene, polyester, polyurethane, nylon or the like. The film passageway 211, 385 in various embodiments may be constructed of or may include a thin film or a woven fabric. The film passageway 211, 385 in various embodiments is connected at the opposite, first, open end to a first support that is to be disposed externally relative to the patient's body. In various embodiments, the first support 220, 330, 384 is generally circular in shape and in various embodiments may be constructed of a more rigid material than that of the second support, the film passageway or both. As such, in one embodiment, the first support 220, 330, 384 is made of a material that is different from the film passageway, the second support or both. In accordance with various embodiments, the first support 220, 330, 384 is shaped or dimensioned to prevent rotation of the first support or twisting of the film passageway. In one embodiment, the first support 220, 330, 384 is shaped to not permit rolling or rotational movement about itself. In accordance with various embodiments, the first support 230, 330, 384, the second support 220, 330, 383, the film passageway 211, 385 or any combination thereof are not inflatable or include an inflatable or fillable bladder. As such, the profile of the trocar surgical seal can remain low and proximate to the body wall and thereby reduce or prevent port crowding or clashing and increase the ability to move or angle an instrument off axis. Additionally, the trocar surgical seal can resist or prevent retraction or retracting of the body wall or the access platform that may cause leak paths or weaken the intended instrument seal.

In accordance with various embodiments, the film passageway 211, 385 is made of material, e.g., polyolefin, or has a thickness, e.g., between 0.0005 to 0.002 inches, that prevents winding of the film passageway around the first support and prevents the film passageway from retracting the opening in the patient's body. In one embodiment, the film passageway 211, 385 has different shapes in an unconstrained condition. In one embodiment, the film passageway 211, 385 is made of a material that is puncture resistant and/or low friction. The width of the working or access channel 360 or the inner diameter of the film passageway 211, 385 in one embodiment are dimensioned to minimize the drag or friction forces associated with insertion, movement, and withdrawal of instruments.

In various embodiments, a valve may be inserted or connected to the first support 230, 330, 384 and comprises a pressure-driven seal that closes upon itself when a pressure differential exists. In various embodiments, the access device 200, 300, 380 may include a zero seal, such as a duck-bill or double duck-bill seal, to prevent back-flow of gas or fluids. In accordance with various embodiments, a zero seal is connected to the first support 230, 330, 384 or the film passageway 211, 385. In accordance with various embodiments, a zero seal is connected to the second support 220, 330, 383. The zero seal in various embodiments comprises an elastomeric material for example at least one polymer resin, rubber, synthetic rubber, polyisoprene, silicone, as well as blends, mixtures, copolymers or composites thereof. In one embodiment, the zero seal is made of a material that is different from the material of the shield, the film passageway, the first support, the second support or any combination thereof.

In accordance with various embodiments, an outer surface area of the film passageway 211, 385 in contact with the patient's body or an access platform is greater than an inner surface area of the film passageway in contact with an inserted instrument. In accordance with various embodiments, the film passageway is constructed to exhibit a predefined shape, such as an hour-glass shape as viewed from the side. The throat or narrowest point along the film passageway's path is sized and configured to represent the instrument-size range for the access device itself. For instance, a throat size of 5.5 mm will accommodate 5 mm instruments. This dedicated profile and throat size can obviate the need for a primary instrument seal because the constrictive pressure on the film passageway from the tissue or wall through which it is inserted compresses the film passageway's material upon the outer surface of the inserted instrument shaft.

In accordance with various embodiments, the film passageway 211, 385 has a length with a range of sizes of 1.5"-4.5". In one embodiment, the film passageway 211, 385 has a length that accommodates different thicknesses of a patient's abdominal wall and in one embodiment a variety of sizes are provided, e.g., small (1.5"-2.5"); medium (2.5"-3.5"); and large (3.5"-4.5"). In one embodiment, the film passageway 211, 385 has a maximum inner diameter of 17 mm, an outer diameter greater than 17 mm or both. In one embodiment, the film passageway 211, 385 has an inner diameter of about 5-7 mm, an outer diameter greater than 7 mm, and/or first and/or second supports having diameters of about 10-12 mm to support 7 mm or smaller instruments. In one embodiment, the film passageway 211, 385 has an inner diameter of about 5-13 mm, an outer diameter greater than about 13 mm, and/or first and/or second supports having inner diameters of about 15-17 mm to support 13 mm or smaller instruments. In one embodiment, the film passageway 211, 385 has an inner diameter of about 5-17 mm, an outer diameter greater than about 17 mm, and/or first and/or second supports having inner diameters of about 20-24 mm to support 17 mm or smaller instruments. In one embodiment, the film passageway 211, 385 is impregnated or otherwise incorporated with antibacterial or antimicrobial agents, coating, particles, laminations or other compositions such as iodine, antibiotics, silver, triclosan, biocides or combinations thereof.

In accordance with various embodiments, the first, external support 230, 306, 384 may comprise a molded elastomeric double duck-billed valve having an integral support or ring associated with the open or proximal end. The double-duck-billed valve provides protection from a sharp or pointed instrument. If the sharp or pointed tip is inadvertently directed toward the side wall of the access device, the tip will be deflected by the valve away from the wall and towards the center or throat portion of the film passageway.

The double-duck-billed valve in various embodiments has a substantially conical overall shape as it is viewed from the side. As viewed from the open, proximal end, the circular shape of the proximal end is resolved into two crossing flat sealing portions. When there is more pressure on the external surface of the valve than on the internal surface, the valve is urged to close. When an instrument is inserted into the valve, the valve does not resist the instrument or present inordinate friction upon the motion of the instrument. In various embodiments, the double-duck-billed valve may include one or more guard members that conform to the internal shape of the valve. This embodiment provides additional protection for the sheath during insertion of sharp or pointed instruments.

In accordance with various embodiments, a dilator may be associated with the open, proximal end of the trocar surgical seal 200, 300, 380 that assists in the opening of the narrow portion of the sheath or film passageway. In various embodiments, one or more dilators or portions thereof are urged forward by the off-axis insertion of an approaching instrument tip to provide a clear and corrected path for the incoming instrument. The one or more dilators or portions thereof subsequently retract when the instrument is in place. A compressive force upon the one or more dilators or portions thereof while within the channel, e.g., an hour-glass shaped channel, of the film passageway urges the one or more dilators or portions thereof proximally and out of the channel.

In accordance with various embodiments, the film passageway 211, 385 is collapsed prior to insertion into the patient's body and remains collapsed in an operational state when no instrument is within the film passageway. In accordance with various embodiments, an insertion or placement device is provided having a handle to be held by a surgeon, an elongate shaft and a distal portion sized and configured to engage the first, inner support of the trocar surgical seal and provide or restrain the support with a shape and profile for insertion through a body wall and into a body cavity. In various embodiments, the insertion device may include one or more retainers, e.g., two distal opposing retainers that engage the first support 230, 306, 384 and stretch the support into an oval or elongate shape. The retainers in various embodiments may include opposing hooks and in various embodiments one or more of the hooks may be alternately moved toward each other or apart from each other.

In accordance with various embodiments, an opening of the access platform in contact with the film passageway 211, 385 exerts a radial or circumferential compressive force that is greater than a drag force of an instrument inserted through the film passageway. In accordance with various embodiments, the access platform has an outer diameter at least two times larger than a maximum inner diameter of the film passageway with an instrument inserted therethrough. In accordance with various embodiments, the opening in the access platform is preformed or made upon insertion of the second support being inserted through the access platform and in accordance with various embodiments the access platform comprises a gel material coupled to a cap or support ring. In accordance with various embodiments, the trocar surgical seal 200, 300, 380 lacks a seal housing, a cannula or retractor.

As shown in various embodiments, a trocar surgical seal 200, 300, 380 is provided for use in a surgical procedure and in particular a minimally invasive procedure. The trocar surgical seal seals a working channel provided by the surgical access device thereby preventing the escape or facilitating the supply of insufflation gases prior to or during a surgical procedure. The trocar surgical seal can seal the working channel with an instrument disposed through the seal and in accordance with various embodiments in the absence of such an instrument. The working channel provides a path or access into a patient's body cavity. The trocar surgical seal in accordance with various embodiments includes multiple layers or components having different characteristics to facilitate or enhance the sealing characteristics of the seal to seal the working channel of the surgical access device.

The trocar surgical seal 200, 300, 380 sealingly engages surgical instruments of various diameters to prevent loss of pneumoperitoneum or to prevent loss of carbon dioxide or other surgical gas during use of such instruments in a laparoscopic procedure. The trocar surgical seal also facilitates the insertion and manipulation of laparoscopic instruments by directing away from the body wall and the body or wall of the surgical seal and by minimizing the friction produced between the surgical seal and the inserted instruments. The trocar surgical seal provides a positive seal with respect to instruments inserted through the trocar surgical seal to prevent loss of pneumoperitoneum during laparoscopic surgical procedures. In various embodiments, in the absence of an inserted instrument, the insufflated abdominal pressure or peritoneal pressure, which typically ranges from 6.5 mm Hg to 17 mm Hg, forces or assists in forcing the film passageway together to sealingly close the instrument channel to prevent loss or leakage of pneumoperitoneum. Pneumoperitoneum pressure in accordance with various embodiments also further forces or assists in forcing the film passageway to form around the shaft of an inserted instrument to prevent excessive loss of carbon dioxide or other insufflation gas. In accordance with various embodiments, the access device 200, 300, 380 can be inserted into a body cavity that is not insufflated or under pneumoperitoneum pressure. In some embodiments, a patient's bone structures, such as the ribs or other such bodily structures, provide radial or circumferential compressive forces that collapse the film passageway of the trocar surgical seal 200, 300, 380.

In accordance with various embodiments, the use of a trocar surgical seal or surgical access device 200, 300, 380 can dramatically reduce the number of components used to achieve instrument access and pneumo-sealing. Often trocars and trocar seals are complicated, have large profiles both in diameter and height off the patient, and are of a fixed rigid diameter. In various embodiments, the trocar surgical seal also conforms to the tissue and is thereby less traumatic. The low profile of the trocar surgical seal or access device also reduces "port crowding". An obturator or introducer in various embodiments eases placement of the access device. The obturator or introducer in various embodiments may be loaded with multiple access devices, staged up behind each other, collapsed longitudinally and/or radially, axially down the shaft of the introducer and deployed one-by-one for multiple access sites. In various embodiments, the access device 200, 300, 380 may also accommodate various instrument sizes as opposed to fixed-size or rigid cannulas. In accordance with various embodiments, the trocar surgical seal 200, 300, 380 is a replacement for typical trocars including seal housings, cannulas and other surgical access devices or platforms or facilitates the use or operation of other surgical access devices or access platforms.

Although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. As such, it should be appreciated that although specific combinations of embodiments and features or aspects of various embodiments may not be explicitly described such combinations however are contemplated and within the scope of the present inventions. Thus, it is intended that the scope of the present inventions herein disclosed should not be limited by the particular disclosed embodiments described above, but should be determined only by a fair reading of the claims.

The invention claimed is:

1. A trocar surgical seal system comprising:
    a proximal bolster;
    a double-duckbilled elastomeric seal connected to the proximal bolster;
    a distal support ring;
    a radially collapsible film passageway with a proximal end connected to the proximal bolster, a distal end connected to the distal support ring, and a longitudinal axis extending from the proximal end to the distal end, the radially collapsible film passageway having an inner surface and an outer surface; and
    an access platform comprising:
        a retractor having a tension-able and elongate tube with an inner support ring arranged to be disposed within the patient; and
        a sealing cap removably coupled to the retractor; and
    wherein the proximal bolster is disposed above and external to the sealing cap and the distal support ring is removably insertable through an opening in the sealing cap, to be positioned under the sealing cap and the film passageway is in direct contact with the opening in the sealing cap, the double-duckbilled elastomeric seal preventing gas from leaking from the distal support ring, through the film passageway and out the proximal bolster and the film passageway providing a zero seal due to compressive forces applied by the sealing cap in direct contact with the film passageway.

2. The system of claim 1 wherein the proximal end of the radially collapsible film passageway is sealingly enclosed in the proximal bolster and the double-duckbilled elastomeric seal is disposed within an inner periphery of the proximal bolster, the proximal bolster being positioned between and separating the double-duckbilled elastomeric seal from the proximal end of the radially collapsible film passageway enclosed in proximal bolster.

3. The system of claim 2 further comprising a single fluid connector attached to the proximal bolster, the single fluid connector having an inlet and an outlet aligned with the inlet, the inlet and outlet facing in a direction perpendicular to the longitudinal axis of the radially collapsible film passageway.

4. The system of claim 3 wherein the radially collapsible film passageway comprises a tubular body having an inner wall being the inner surface of the radially collapsible film and an outer wall being the outer surface of the radially collapsible film passageway and further comprising a single fluid connector attached to the proximal bolster and a single fluid channel extending through the proximal bolster, between inner and outer walls of the radially collapsible film passageway and out through a plurality of holes at the distal end of the radially collapsible film passageway.

5. The system of claim 4 wherein the plurality of holes face in a direction perpendicular to the longitudinal axis of the radially collapsible film passageway.

6. The system of claim 1 further comprising a surgical instrument, the surgical instrument insertable through the double-duckbilled elastomeric seal, the radially collapsible film passageway and the distal support ring.

7. The system of claim 4 wherein the radially collapsible film passageway has a non-adjustable length, the length being between 1.5 inches to 4.5 inches with an outer surface of a shaft of the surgical instrument being in direct contact with and sealing against the inner surface of the radially collapsible film passageway.

8. The system of claim 7 further comprising a coefficient of friction between the thin radially collapsible film and the outer surface of the inserted instrument in direct contact with the inner surface of the thin radially collapsible film being less than a coefficient of kinetic friction between the double-duckbilled elastomeric seal and the outer surface of the inserted instrument in direct contact with the double-duckbilled elastomeric seal.

9. The system of claim 7 wherein the radially collapsible film passageway is thin having a thickness between 0.0005 to 0.002 inches that is not able to extend in a longitudinal direction and resists forces to stretch the radially collapsible film passageway in a longitudinal direction.

10. The system of claim 9 wherein the proximal bolster has a length greater than a length of the distal support ring and smaller than a length of the thin radially collapsible film.

* * * * *